(12) United States Patent
Chang et al.

(10) Patent No.: US 12,661,001 B2
(45) Date of Patent: Jun. 23, 2026

(54) ESTABLISHING METHOD OF RETINAL LAYER AUTO-SEGMENTATION MODEL, RETINAL LAYER QUANTIFICATION SYSTEM, EYE CARE DEVICE, METHOD FOR DETECTING RETINAL LAYER THICKNESS AND RETINAL LAYER AREA, AND METHOD FOR ASSESSING AND PREDICTING NEURODEGENERATIVE DISEASE

(71) Applicant: Chi Mei Medical Center, Tainan City (TW)

(72) Inventors: Ching-Ping Chang, Tainan City (TW);
Jia-Yi Hong, Tainan City (TW);
Shu-Chun Kuo, Tainan City (TW);
Jui-Ti Ma, Tainan City (TW);
Chung-Hsin Tseng, Tainan City (TW)

(73) Assignee: Chi Mei Medical Center, Tainan City (TW)

( * ) Notice: Subject to any disclaimer, the term of this patent is extended or adjusted under 35 U.S.C. 154(b) by 515 days.

(21) Appl. No.: 18/337,448

(22) Filed: Jun. 20, 2023

(65) Prior Publication Data
US 2024/0180415 A1 Jun. 6, 2024

(30) Foreign Application Priority Data
Dec. 6, 2022 (TW) .................................. 111146819

(51) Int. Cl.
*G06T 7/13* (2017.01)
*A61B 3/00* (2006.01)
*A61B 3/10* (2006.01)
(52) U.S. Cl.
CPC ............ *A61B 3/0025* (2013.01); *A61B 3/102* (2013.01); *G06T 7/13* (2017.01); *G06T 2207/30041* (2013.01)

(58) Field of Classification Search
CPC ......... A61B 3/0025; A61B 3/102; G06T 7/13; G06T 2207/30041; G06T 7/11
See application file for complete search history.

(56) References Cited

U.S. PATENT DOCUMENTS

2021/0158525 A1* 5/2021 Iwase ................... A61B 3/0025
2022/0104703 A1 4/2022 Lambrou
2023/0143051 A1* 5/2023 Bagherinia .......... A61B 3/0025
382/107

FOREIGN PATENT DOCUMENTS

CN 112513999 A 3/2021
CN 114549520 A 5/2022
TW 202203844 A 2/2022

OTHER PUBLICATIONS

Liu, Xiaoming et al. "Shortest Path with Backtracking Based Automatic Layer Segmentation in Pathological Retinal Optical Coherence Tomography Images." Multimedia tools and applications 78.12 (2019): 15817-15838. Web. (Year: 2019).*
(Continued)

*Primary Examiner* — John R Wallace
(74) *Attorney, Agent, or Firm* — CKC & Partners Co., LLC

(57) ABSTRACT
A retinal layer quantification system includes an image capturing unit and a processor electrically connected to the image capturing unit. The image capturing unit is configured to capture a target optical coherence tomographic image of a subject. The processor stores a program including a target image pre-processing module, a retinal layer auto-segmentation model, a target image enhancement module, a layer thickness detection module and a layer area detection module. The program detects a retinal layer thickness and a retinal layer area of the subject when the program is executed by the processor.

13 Claims, 26 Drawing Sheets
(3 of 26 Drawing Sheet(s) Filed in Color)

(56) References Cited

OTHER PUBLICATIONS

Sidiqi, Ahmad et al. "In Vivo Retinal Fluorescence Imaging With Curcumin in an Alzheimer Mouse Model." Frontiers in neuroscience 14 (2020): 713. Web. (Year: 2020).*

* cited by examiner

100

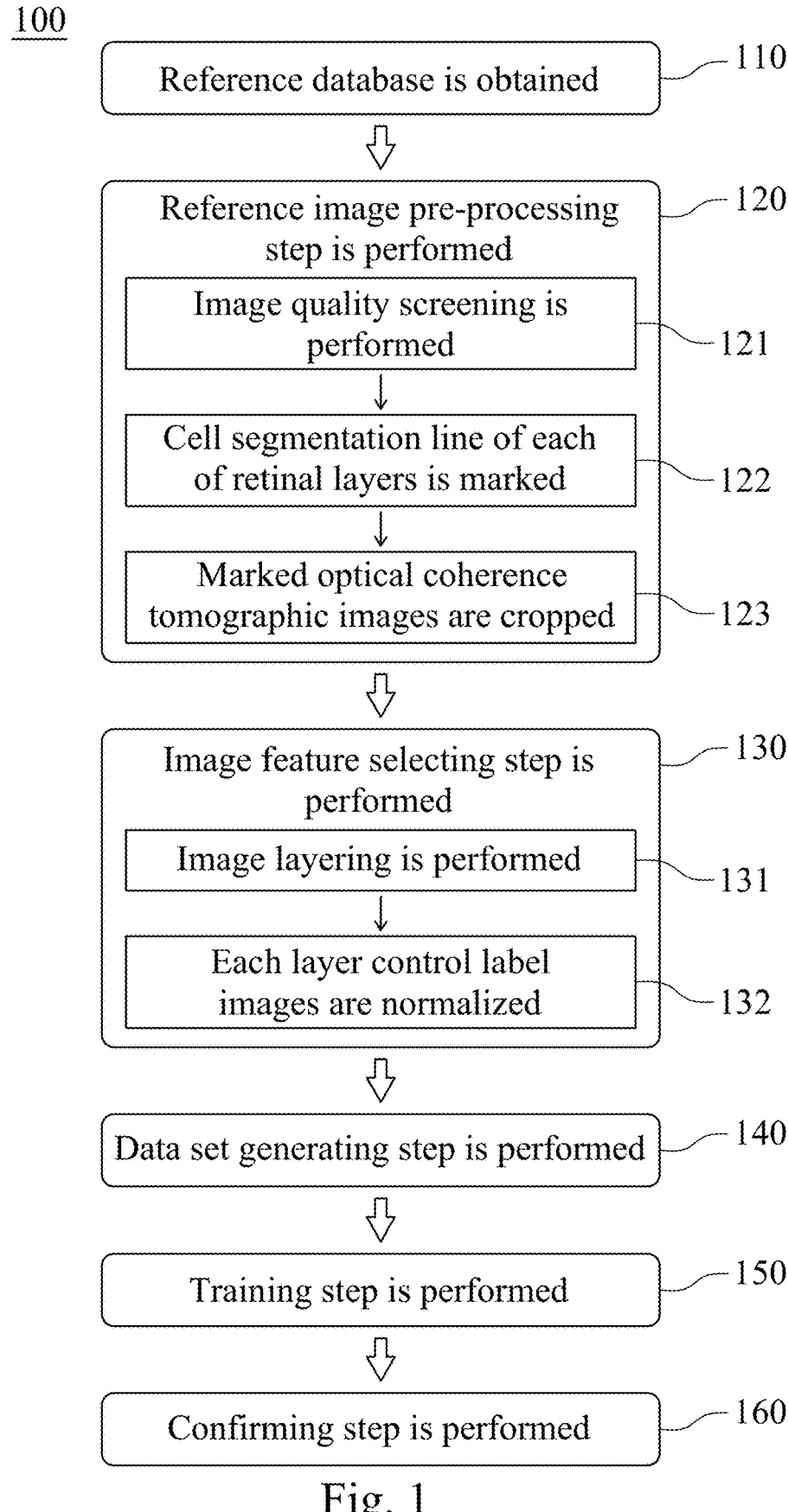

Reference database is obtained —— 110

Reference image pre-processing step is performed —— 120

Image quality screening is performed —— 121

Cell segmentation line of each of retinal layers is marked —— 122

Marked optical coherence tomographic images are cropped —— 123

Image feature selecting step is performed —— 130

Image layering is performed —— 131

Each layer control label images are normalized —— 132

Data set generating step is performed —— 140

Training step is performed —— 150

Confirming step is performed —— 160

131
103
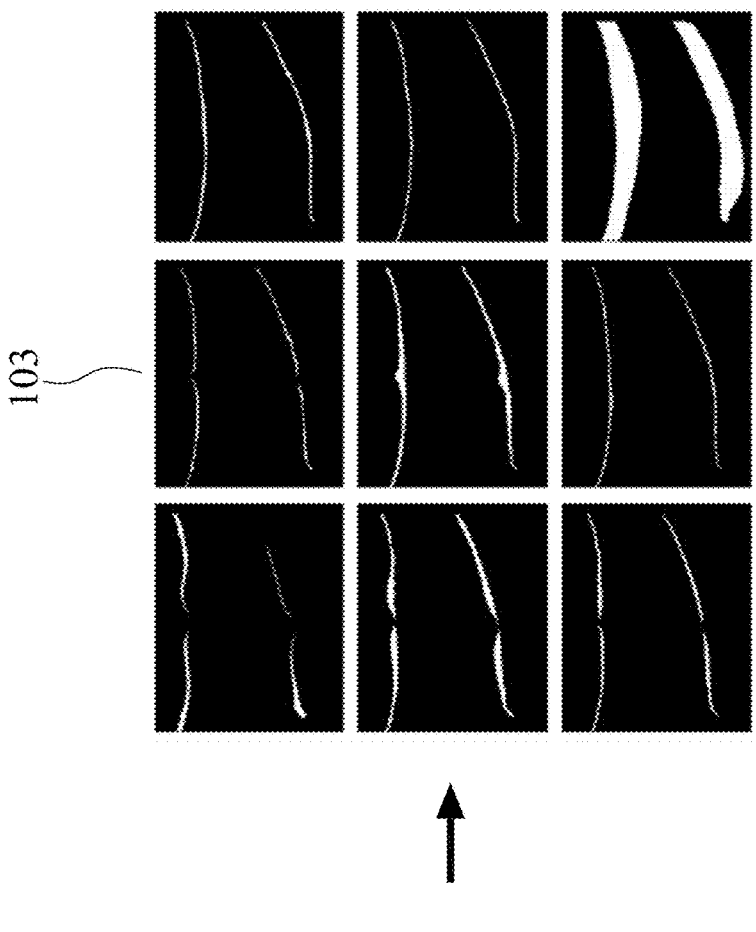
102
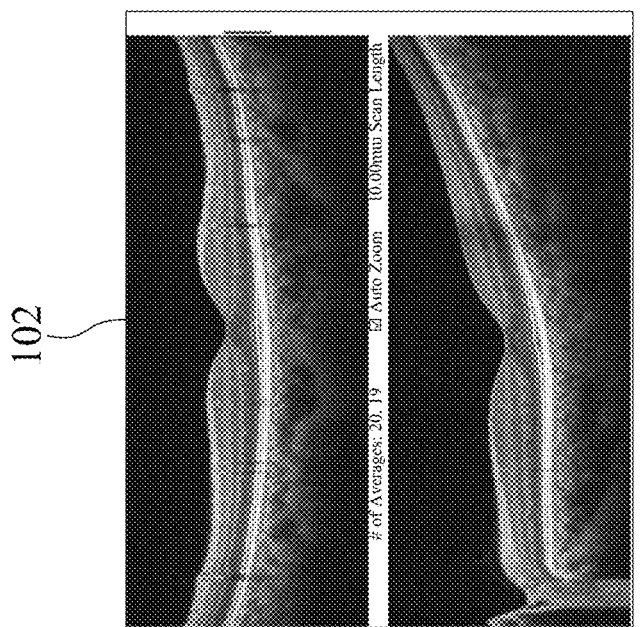
Fig. 2D

132

[213, 205, 205],
[213, 205, 205],
[213, 205, 205],
...,
[186, 184, 176],
[133, 134, 125],
[125, 126, 177]],

[213, 205, 205],
[213, 205, 205],
[213, 205, 205],
...,
[194, 192, 184],
[159, 160, 151],
[112, 113, 104]],

[212, 205, 202],
[212, 205, 202],
[212, 205, 202],

Before normalization

:[0.83529412, 0.80392157, 0.80392157],
[0.83529412, 0.80392157, 0.80392157],
[0.83529412, 0.80392157, 0.80392157],
...,
[0.72941176, 0.72156863, 0.69019608],
[0.52156863, 0.5254902 , 0.49019608],
[0.49019608, 0.49411765, 0.45882353]],

:[0.83529412, 0.80392157, 0.80392157],
[0.83529412, 0.80392157, 0.80392157],
[0.83529412, 0.80392157, 0.80392157],
...,
[0.76078431, 0.75294118, 0.72156863],
[0.62352941, 0.62745098, 0.59215686],
[0.43921569, 0.44313725, 0.40784314]],

:[0.83137255, 0.80392157, 0.79215686],
[0.83137255, 0.80392157, 0.79215686],
[0.83137255, 0.80392157, 0.79215686],
...,
[0.74117647, 0.73333333, 0.70196078],
[0.81176471, 0.81568627, 0.78039216],
[0.69019608, 0.69411765, 0.65882353]]],

Before normalization

140

Image Flip

Image Translation

Adjustment of
Brightness

Adjustment of
Brightness

570

Horizontal retinal segmentation and vertical retinal segmentation are performed — 571

⇨

Horizontal retinal layer area and vertical retinal layer area are calculated — 572

563

571

572

Calculate how many white points in total

Calculate with square area formula 1 pixel

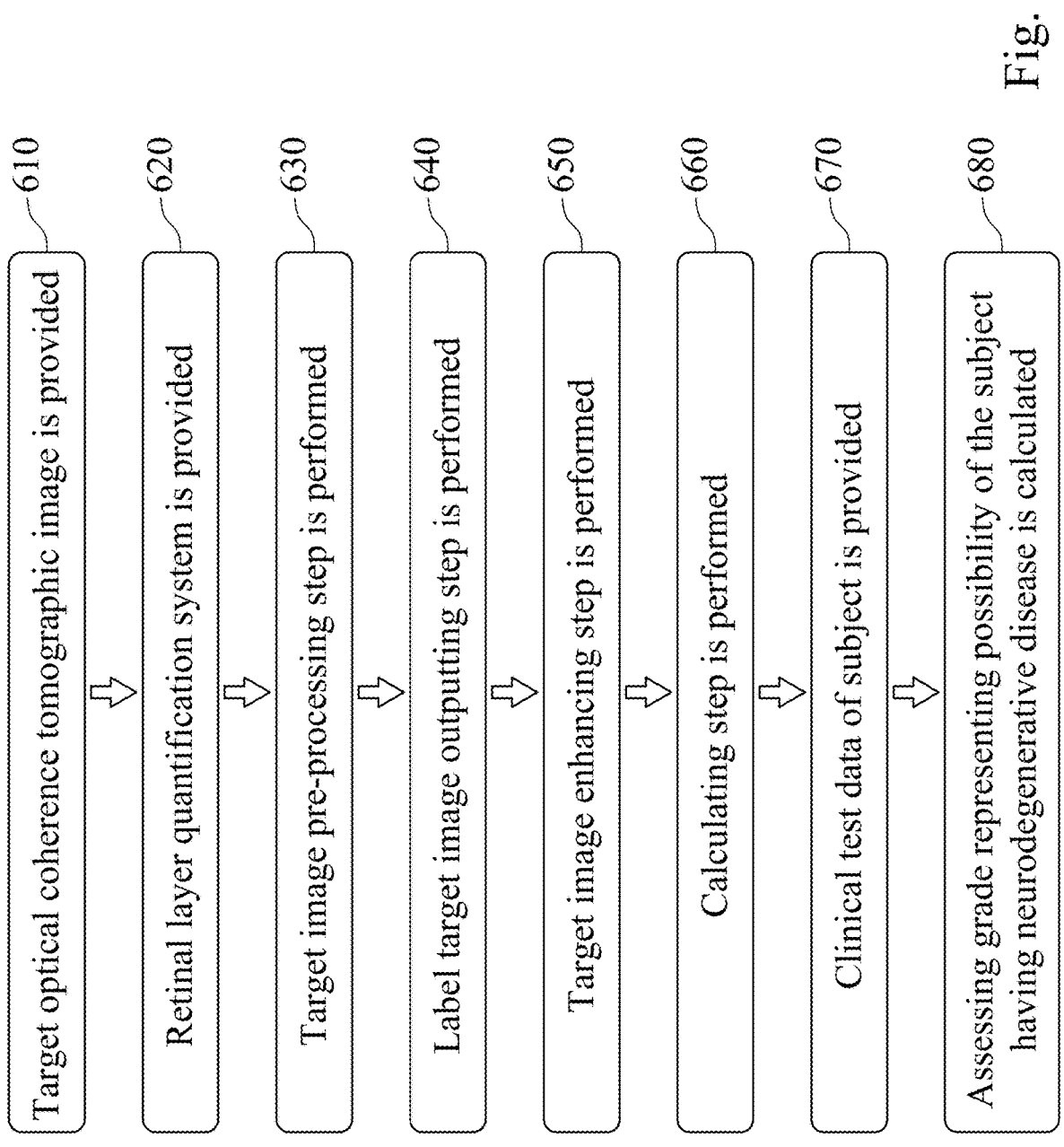

610   Target optical coherence tomographic image is provided

620   Retinal layer quantification system is provided

630   Target image pre-processing step is performed

640   Label target image outputting step is performed

650   Target image enhancing step is performed

660   Calculating step is performed

670   Clinical test data of subject is provided

680   Assessing grade representing possibility of the subject having neurodegenerative disease is calculated

ESTABLISHING METHOD OF RETINAL LAYER AUTO-SEGMENTATION MODEL, RETINAL LAYER QUANTIFICATION SYSTEM, EYE CARE DEVICE, METHOD FOR DETECTING RETINAL LAYER THICKNESS AND RETINAL LAYER AREA, AND METHOD FOR ASSESSING AND PREDICTING NEURODEGENERATIVE DISEASE

RELATED APPLICATIONS

This application claims priority to Taiwan Application Serial Number 111146819, filed Dec. 6, 2022, which is herein incorporated by reference.

BACKGROUND

Technical Field

The present disclosure relates to a medical information analysis model, system and method. More particularly, the present disclosure relates to a retinal layer auto-segmentation model, a retinal layer quantification system, an eye care device, a method for detecting retinal layer thickness and retinal layer area and a method for assessing and predicting neurodegenerative disease.

Description of Related Art

The retina is a very thin layer of cells at the back of an eyeball of vertebrates and some cephalopods. The retina includes rod cells and cone cells which can sense light, and the sensed light can be converted into neural signals. The human retina is divided into 11 layers, which are, from the outermost to the innermost, choroid, retinal pigment epithelium, layer of rods and cones, external limiting membrane, outer nuclear layer, outer plexiform layer, inner nuclear layer, inner plexiform layer, ganglion cell layer, nerve fiber layer and inner limiting membrane. Many ophthalmic diseases are accompanied by pathological changes in retinal thickness due to edema or atrophy of the retina. Diseases such as diabetic retinopathy, central serous chorioretinopathy, retinal vascular occlusion, uveitis and cataract extraction may cause macular edema which leads to an increase in retinal thickness. In contrast, retinal atrophy caused by glaucoma and some degenerative diseases may lead to a decrease in retinal thickness. Objective, accurate, and sensitive measurement of retinal thickness has important clinical significance for diagnosis and treatment guidance of these ophthalmic diseases.

In addition, the retina and the central nervous system both originate from the developing neural ectoderm, and maintain a direct and permanent connection through the optic nerve. As an extension of the central nervous system, the retina and the brain share many histological, physiological and embryological features. The changes in retinal structure may reflect the pathological changes in the central nervous system (CNS) of neurodegenerative diseases, such as multiple sclerosis, Parkinson's disease, Alzheimer's disease, stroke, and traumatic encephalopathy, during the progression. Therefore, the segmentation of each layer of the retina is useful for measuring the maximum thickness and cell density of a retinal monolayer for the finest observation. Previous animal or clinical studies have found that some neurodegenerative diseases (such as mild cognitive impairment, Alzheimer's disease, Parkinson's disease, depression, mental illness, multiple sclerosis, muscular dystrophy, lupus erythematosus, phenylketonuria, etc.) patients can detected retinal monolayer thickness change or retinal multilayer thickness change in the optical coherence tomographic image. The use of the optical coherence tomography can avoid human error in diagnosis due to lack of clinical experience, and can achieve the function of early prevention and diagnosis of brain neurodegeneration, thereby reducing the increase in social costs and the generation of medical capacity overload.

At present, the relevant information of the quantitative data of optical coherence tomography imaging instruments used clinically can be obtained mainly by manual segmentation. Manual segmentation not only requires professional judges, it is also pretty time-consuming for clinical use or large-scale multicenter trials. Furthermore, because the determination is subjective, it is easy to make determination error of the result and lose the great opportunity for treatment. In this regard, auto-segmentation and quantification system is a very important issue. Evaluation can be made based on the establishment of a big database after segmentation as well as prognosis and treatment response of the patient, which will be worthy of clinical applications.

SUMMARY

According to an aspect of the present disclosure, an establishing method of a retinal layer auto-segmentation model includes steps as follows. A reference database is obtained, a reference image pre-processing step is performed, an image feature selecting step is performed, a data set generating step is performed, a training step is performed and a confirming step is performed. The reference database includes a plurality of reference optical coherence tomographic images. In the reference image pre-processing step, each of the plurality of reference optical coherence tomographic images is duplicated, a cell segmentation line of each of retinal layers is marked and each of the plurality of reference optical coherence tomographic images is cropped, so as to obtain a plurality of control label images. In the image feature selecting step, each of the plurality of control label images is analyzed by a feature selecting module, and an each layer control label image feature from each of the plurality of control label images is obtained, so as to obtain a plurality of each layer control label image features. In the data set generating step, the reference optical coherence tomographic images and corresponding one of the control label images are processed in a data enhancement method to obtain a data set, and the data set is divided into a training set and a validation set. The data set includes the plurality of reference optical coherence tomographic images, the plurality of control label images, a plurality of adjusted reference optical coherence tomographic images and a plurality of adjusted control label images. In the training step, the training set is trained with the plurality of each layer control label image features through a U-net convolution neural network learning classifier to reach convergence, so as to obtain the retinal layer auto-segmentation model. In the confirming step, a plurality of label reference images from the validation set is outputted using the retinal layer auto-segmentation model, and each of the plurality of label reference images is compared with corresponding one of the plurality of control label images, so as to confirm an accuracy of the retinal layer auto-segmentation model.

According to another aspect of the present disclosure, a retinal layer quantification system includes an image capturing unit and a processor. The image capturing unit is configured to capture a target optical coherence tomographic image of a subject. The processor is electrically connected to the image capturing unit and stores a program, wherein the program detects a retinal layer thickness and a retinal layer area of the subject when the program is executed by the processor. The program includes a target image pre-processing module, a retinal layer auto-segmentation model, a target image enhancement module, a layer thickness detection module and a layer area detection module. The target image pre-processing module is configured to screen and mark the target optical coherence tomographic image, so as to obtain a marked target image. The retinal layer auto-segmentation model is established by the establishing method of the retinal layer auto-segmentation model according to the aforementioned aspect, and the retinal layer auto-segmentation model is used to output the marked target image as a label target image. The target image enhancement module is configured to perform image enhancement on the label target image to obtain an enhanced label target image. The layer thickness detection module is configured to calculate the retinal layer thickness in the enhanced label target image, wherein the retinal layer thickness includes retinal layer each region thicknesses. The layer area detection module is configured to calculate the retinal layer area in the enhanced label target image, wherein the retinal layer area includes a horizontal retinal layer area and a vertical retinal layer area.

According to one another aspect of the present disclosure, an eye care device includes the retinal layer quantification system according to the aforementioned aspect and an electronic device. The electronic device is connected to the retinal layer quantification system through telecommunication.

According to still another aspect of the present disclosure, a method for detecting retinal layer thickness and retinal layer area includes steps as follows. A target optical coherence tomographic image of a subject is provided. The retinal layer quantification system according to the aforementioned aspect is provided. A target image pre-processing step is performed, wherein the target optical coherence tomographic image is screened and marked using the target image pre-processing module, so as to obtain the marked target image. A label target image outputting step is performed, wherein the marked target image is outputted as the label target image using the retinal layer auto-segmentation model. A target image enhancing step is performed, wherein the label target image is processed in an image enhancement method using the target image enhancement module, so as to obtain the enhanced label target image. A layer thickness calculating step is performed, wherein the retinal layer each region thicknesses in the enhanced label target image are calculated using the layer thickness detection module. A layer area calculating step is performed. wherein the horizontal retinal layer area and the vertical retinal layer area in the enhanced label target image are calculated using the layer area detection module.

According to further another aspect of the present disclosure, a method for assessing and predicting neurodegenerative disease includes steps as follows. A target optical coherence tomographic image of a subject is provided. The retinal layer quantification system according to the aforementioned aspect is provided. A target image pre-processing step is performed, wherein the target optical coherence tomographic image is screened and marked using the target image pre-processing module, so as to obtain the marked target image. A label target image outputting step is performed, wherein the marked target image is outputted as the label target image using the retinal layer auto-segmentation model. A target image enhancing step is performed, wherein the label target image is processed in an image enhancement method using the target image enhancement module, so as to obtain the enhanced label target image. A calculating step is performed, wherein the retinal layer each region thicknesses in the enhanced label target image are calculated using the layer thickness detection module, and the horizontal retinal layer area and the vertical retinal layer area in the enhanced label target image are calculated using the layer area detection module. A clinical test data of the subject is provided. The clinical test data is compared with the thickness of each area of retinal layer, the horizontal retinal layer area and the vertical retinal layer area by a regression analysis model, so as to calculate an assessing grade representing a possibility of the subject having neurodegenerative disease.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows:

FIG. 1 is a step flow chart of an establishing method of a retinal layer auto-segmentation model according to an embodiment of the present disclosure.

FIG. 2A, FIG. 2B, FIG. 2C, FIG. 2D, FIG. 2E and FIG. 2F show a schematic diagram of Step 121, Step 122, Step 123, Step 131, Step 132 and Step 140, respectively.

FIG. 5 is a step flow chart of a method for assessing and predicting neurodegenerative disease according to further another embodiment of the present disclosure.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

I. Establishing Method of a Retinal Layer Auto-Segmentation Model

Reference is made to FIG. 1, which is a step flow chart of an establishing method of a retinal layer auto-segmentation model 100 according to an embodiment of the present disclosure. The establishing method of a retinal layer auto-segmentation model 100 includes Step 110, Step 120, Step 130, Step 140, Step 150 and Step 160. The established retinal layer auto-segmentation model can be configured to output label target image, so as to automatically segment retina layers on an optical coherence tomographic (OCT) image.

In Step 110, a reference database is obtained. The reference database includes a plurality of reference optical coherence tomographic images 101.

Figure 2A:
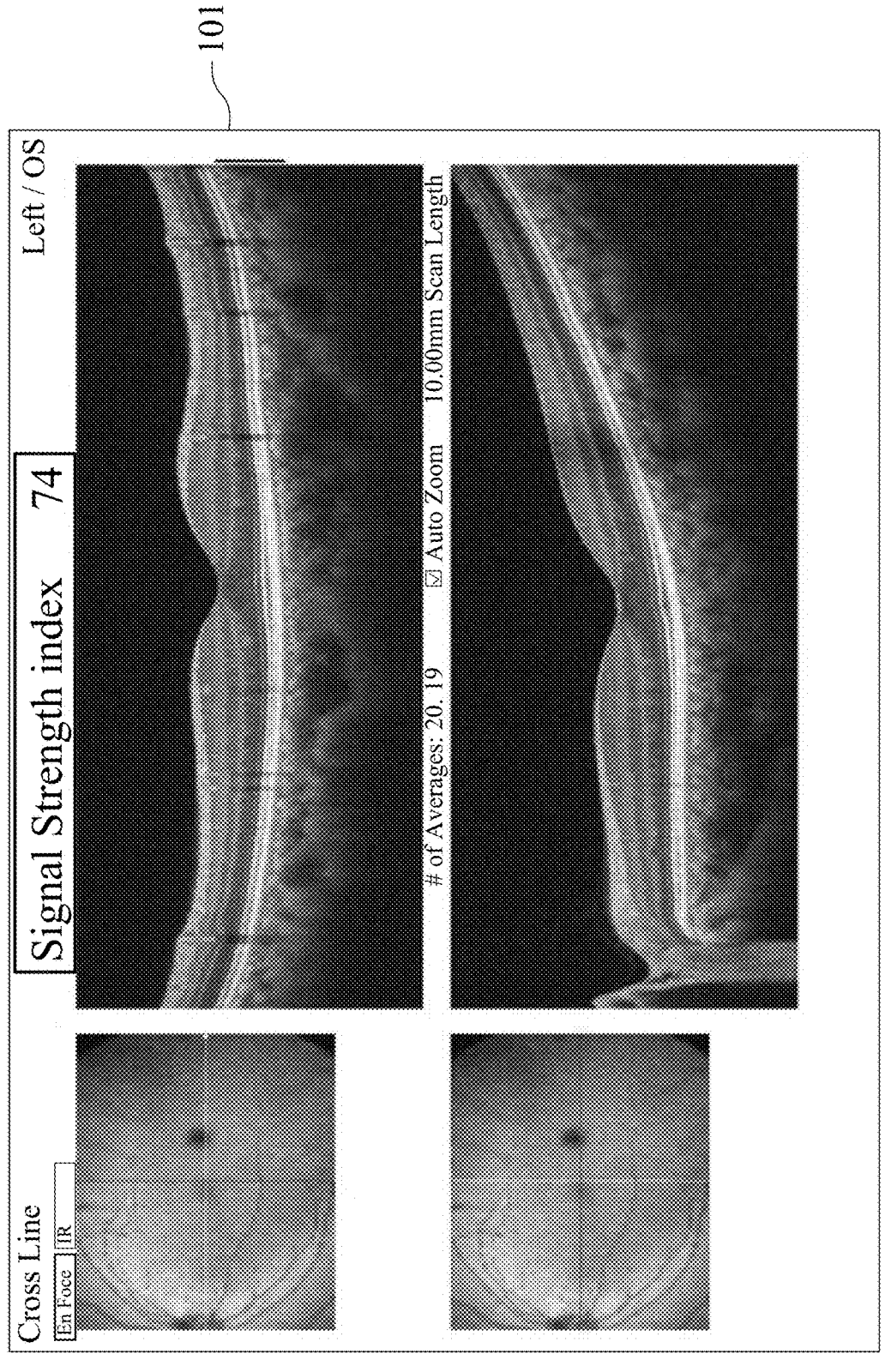
Figure 2B:
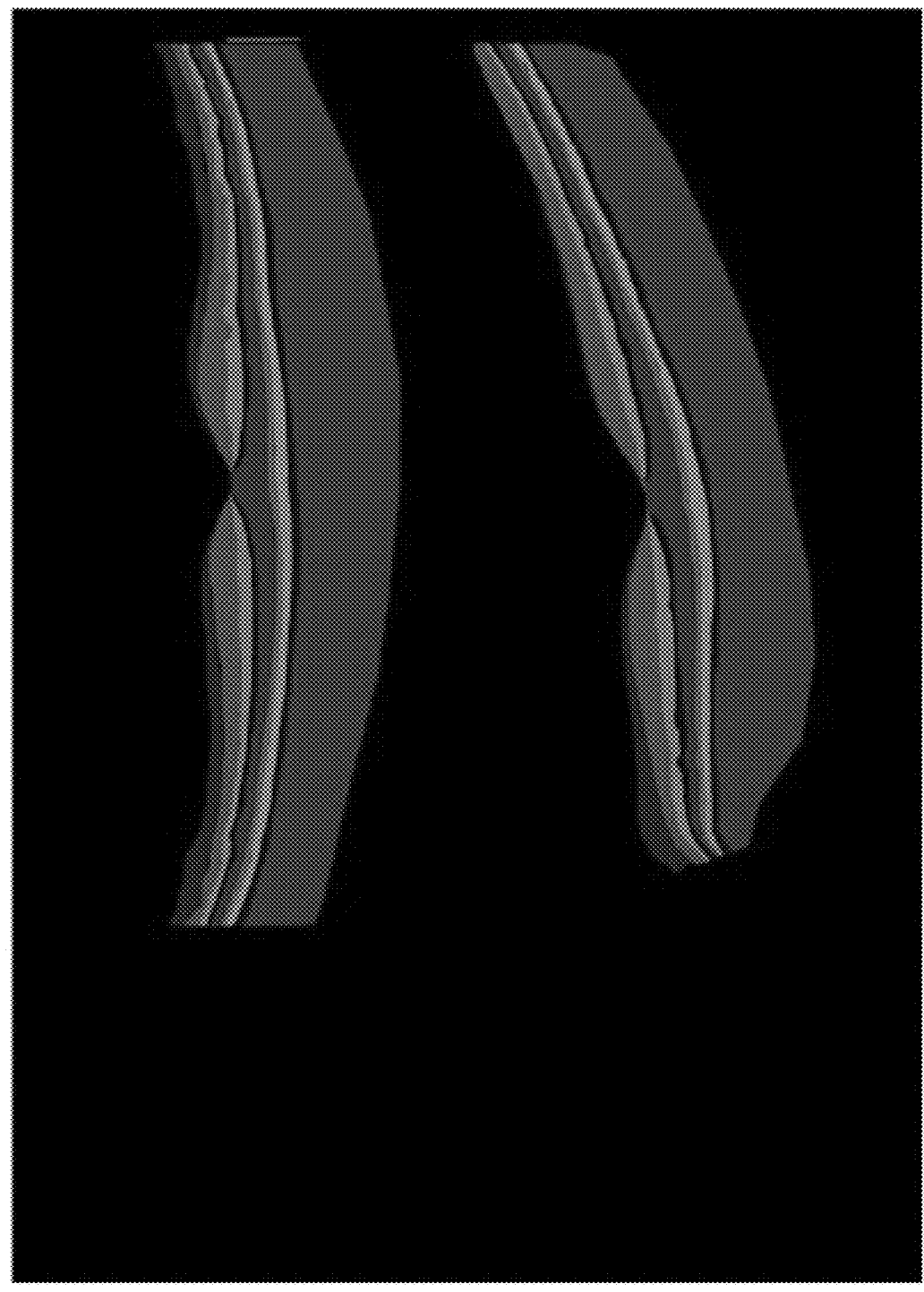
Figure 2C:
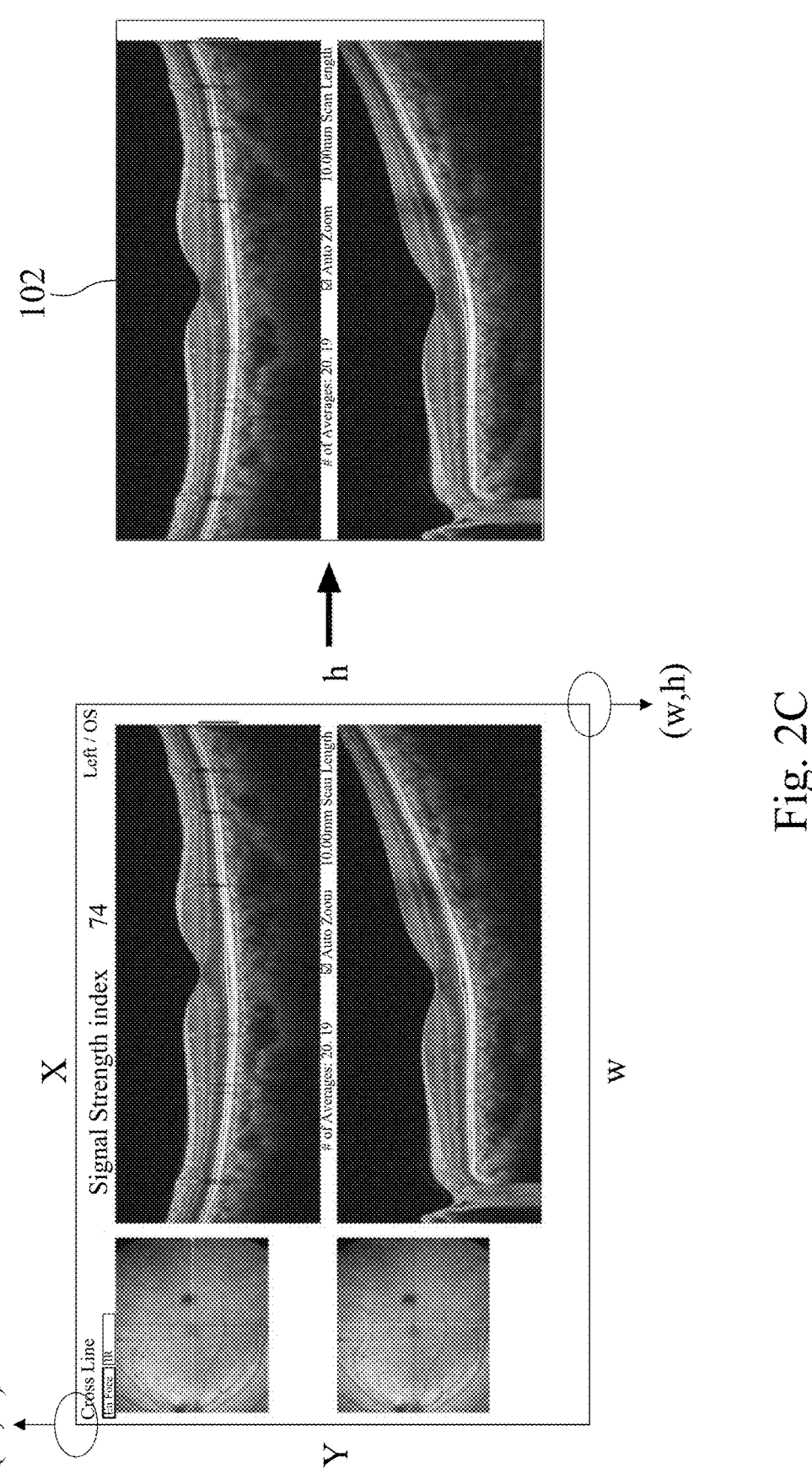

In Step 120, a reference image pre-processing step is performed. Each of the plurality of reference optical coherence tomographic images 101 is duplicated, a cell segmentation line of each of retinal layers is marked and each of the plurality of reference optical coherence tomographic images 101 is cropped, so as to obtain a plurality of control label images. In addition, Step 120 can include Step 121, Step 122 and Step 123. Reference is made to FIG. 2A to FIG. 2C, which show a schematic diagram of Step 121, Step 122 and Step 123 in FIG. 1, respectively.

In Step 121, an image quality screening is performed on the plurality of reference optical coherence tomographic images 101, and the plurality of reference optical coherence tomographic images 101 meeting an image quality are retained. As shown in FIG. 2A, a "Signal Strength index" is displayed in the plurality of reference optical coherence tomographic images 101. In Step 121, the value of the Signal Strength index in the plurality of reference optical coherence tomographic images 101 above 50 is selected for subsequent model building.

In Step 122, the cell segmentation line of each of retinal layers in each of the plurality of reference optical coherence tomographic images 101 is marked, so as to obtain a plurality of marked optical coherence tomographic images. The obtained marked optical coherence tomographic image is shown in FIG. 2B.

In Step 123, the plurality of marked optical coherence tomographic images are cropped respectively, so as to obtain the plurality of control label images 102. As shown in FIG. 2C, the coordinate information (X, Y) of the upper left vertex of the marked optical coherence tomographic image and the width and height (w, h) of the marked optical coherence tomographic image are used as the reference for cropping unnecessary information, so as to obtain the control label images 102.

Figures 2E, 2F:
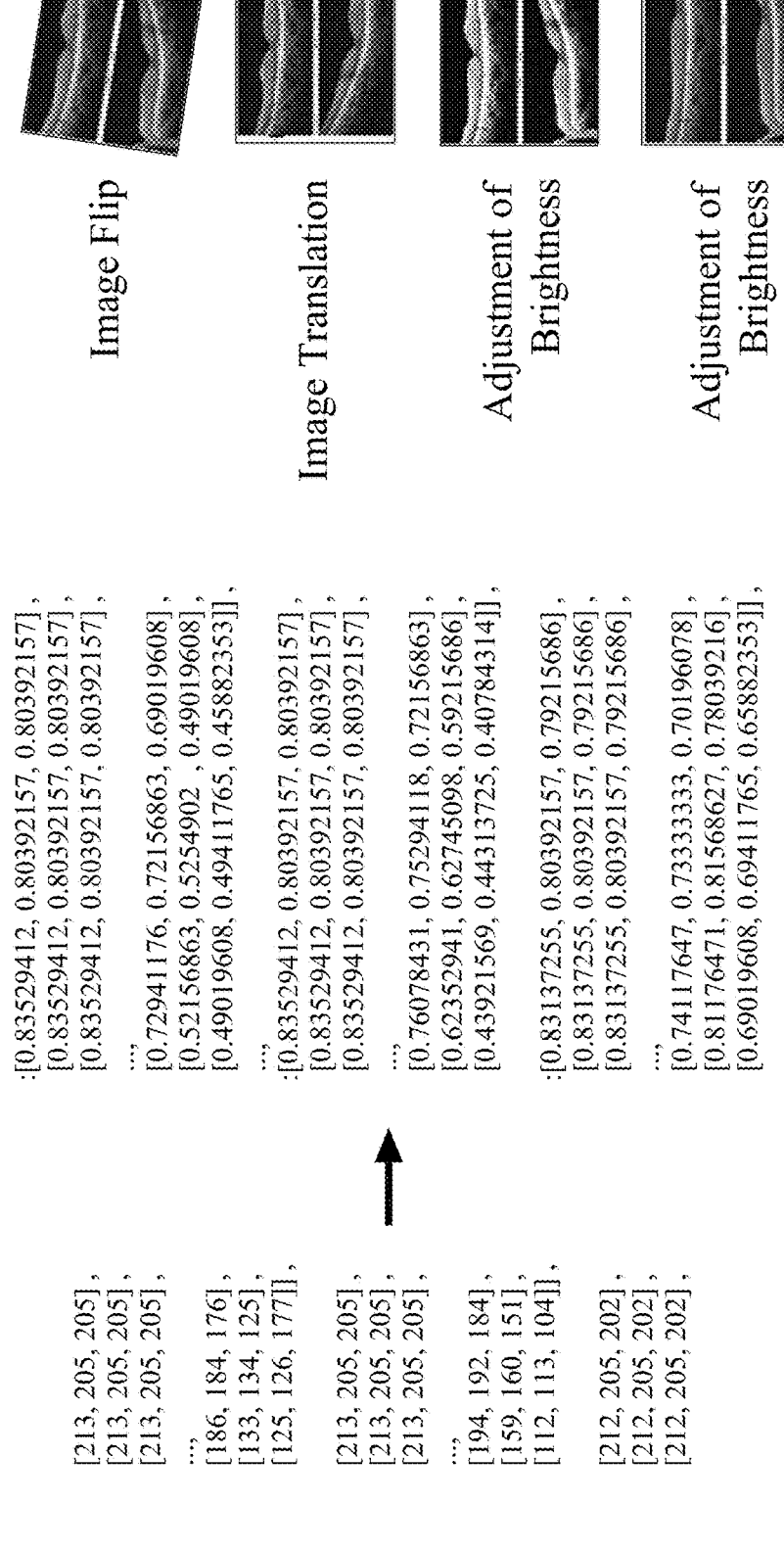

In Step 130, an image feature selecting step is performed. Each of the plurality of control label images 102 is analyzed by a feature selecting module, and an each layer control label image feature from each of the plurality of control label images 102 is obtained, so as to obtain a plurality of each layer control label image features. In addition, Step 130 can include Step 131 and Step 132. Reference is made to FIG. 2D and FIG. 2E, which show a schematic diagram of Step 131 and Step 132 in FIG. 1, respectively.

In Step 131, an image layering is performed on each of the plurality of control label images 102 to obtain a plurality of each layer control label images 103. As shown in FIG. 2D, each of the plurality of each layer control label images 103 includes 9 retinal monolayer images.

In Step 132, the plurality of each layer control label images 103 are normalized, so as to obtain the plurality of each layer control label image features. As shown in FIG. 2E, the plurality of each layer control label image features are compressed to between 0 and 1 after normalization. That is, all black is displayed as 0, and all white is displayed as 1, so that the plurality of each layer control label image features still have a degree of discrimination. Normalization can greatly reduce the amount of data processing to reduce the burden on hardware devices.

In Step 140, a data set generating step is performed. The plurality of reference optical coherence tomographic images 101 and corresponding one of the control label images 102 are processed in a data enhancement method to obtain a data set, and the data set is divided into a training set and a validation set. The data set includes the plurality of reference optical coherence tomographic images 101, the plurality of control label images 102, a plurality of adjusted reference optical coherence tomographic images and a plurality of adjusted control label images. Reference is made to FIG. 2F, which show a schematic diagram of Step 140 in FIG. 1. In FIG. 2F, the data enhancement method can include an image flip, an image translation, an adjustment of brightness and an adjustment of scale.

In Step 150, a training step is performed. The training set is trained with the plurality of each layer control label image features through a U-net convolution neural network learning classifier to reach convergence, so as to obtain the retinal layer auto-segmentation model. The U-net convolution neural network learning classifier can include 4 times of downsampling and 4 times of upsampling.

In Step 160, a confirming step is performed. A plurality of label reference images from the validation set is outputted using the retinal layer auto-segmentation model, and each of the plurality of label reference images is compared with corresponding one of the plurality of control label images, so as to confirm an accuracy of the retinal layer auto-segmentation model.

II. Retinal Layer Quantification System

Figure 3A:
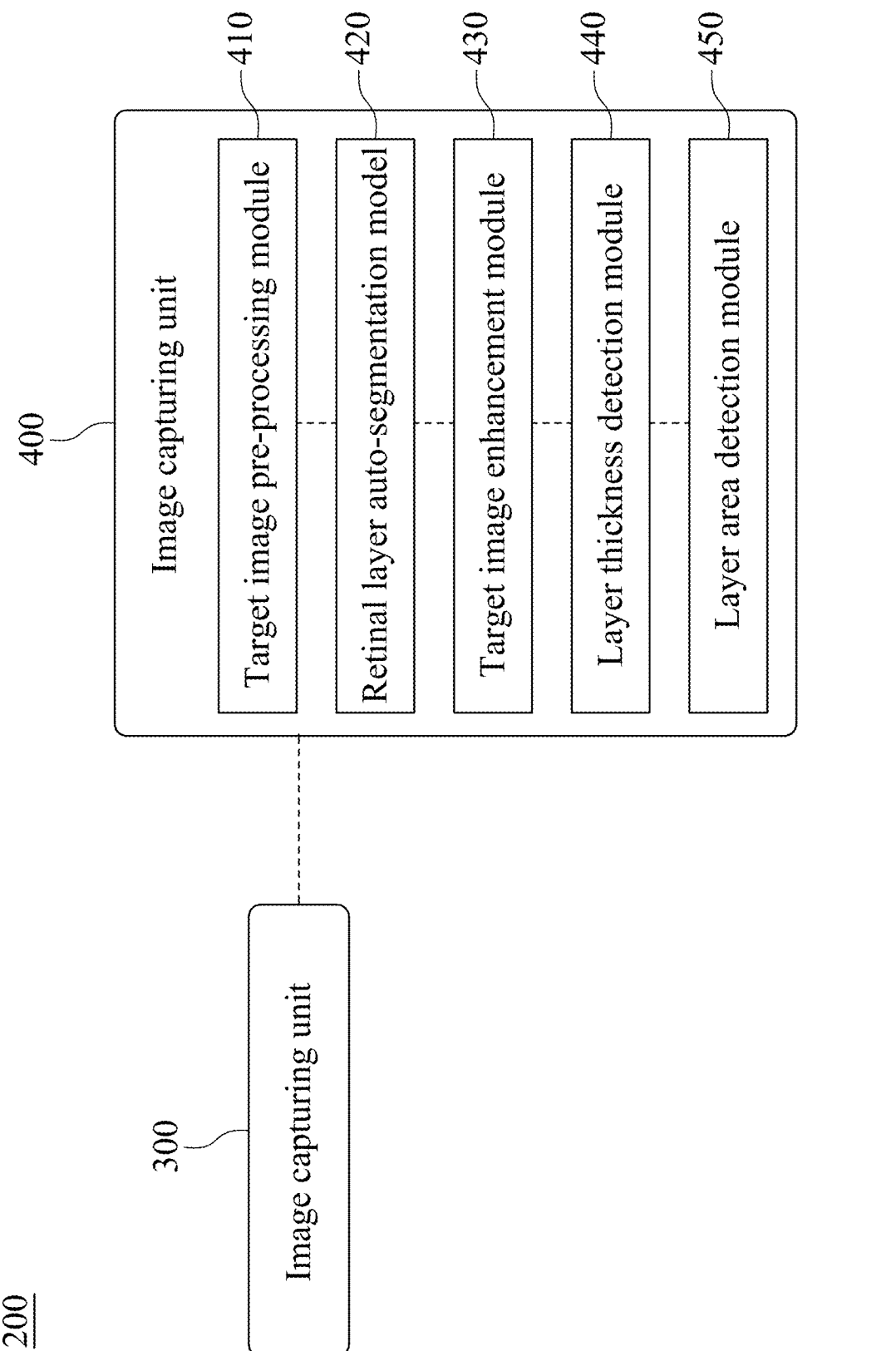
FIG. 3A is a structural schematic view of a retinal layer quantification system according to another embodiment of the present disclosure.
Figures 3B, 3C, 3D:
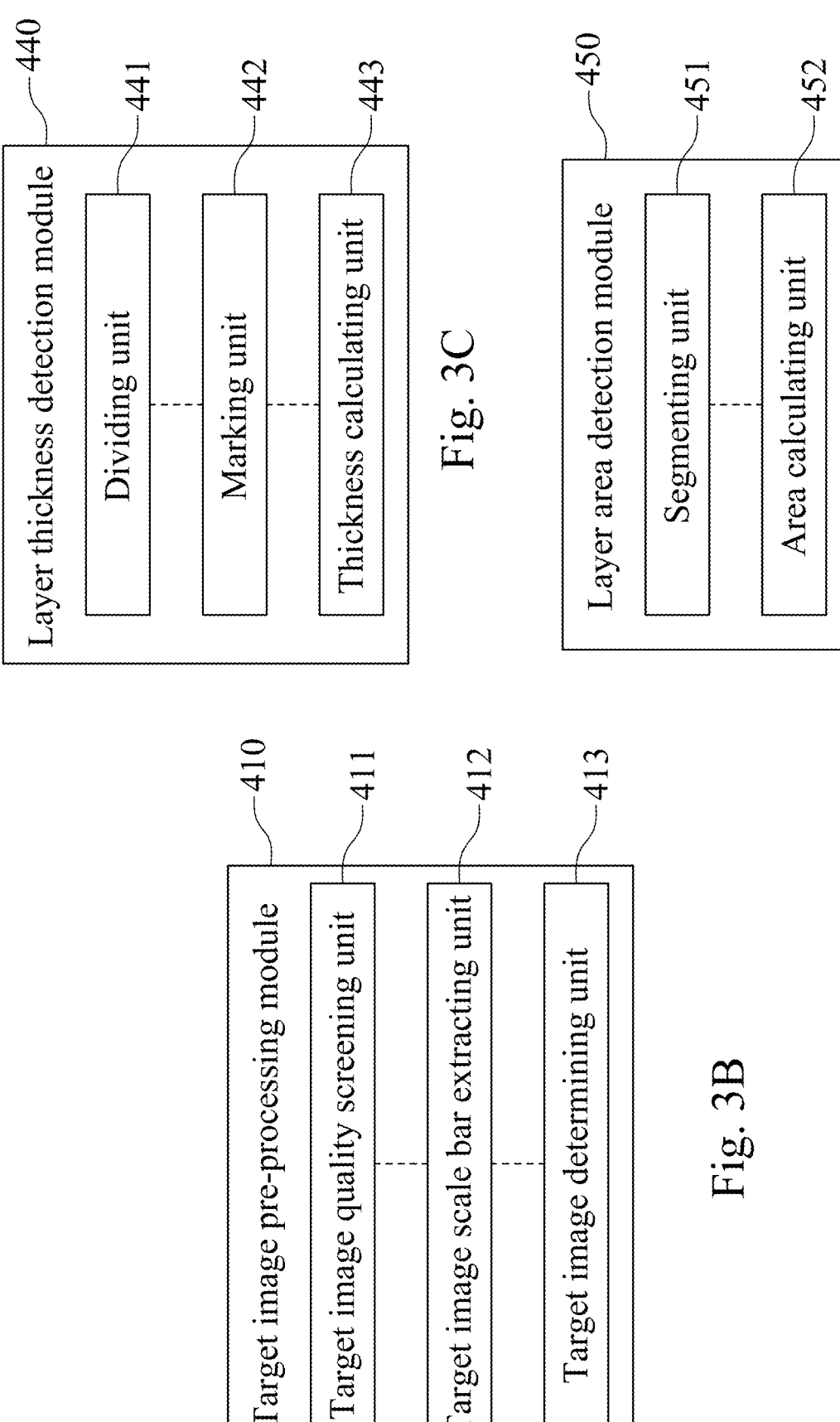
FIG. 3B is a structural schematic view of a target image pre-processing module in FIG. 3A.
FIG. 3C is a structural schematic view of a layer thickness detection module in FIG. 3A.
FIG. 3D is a structural schematic view of a layer area detection module in FIG. 3A.

Reference is made to FIG. 3A to FIG. 3D. FIG. 3A is a structural schematic view of a retinal layer quantification system 200 according to another embodiment of the present disclosure. FIG. 3B is a structural schematic view of a target image pre-processing module 410 in FIG. 3A. FIG. 3C is a structural schematic view of a layer thickness detection module 440 in FIG. 3A. FIG. 3D is a structural schematic view of a layer area detection module 450 in FIG. 3A.

The retinal layer quantification system 200 includes an image capturing unit 300 and a processor 400. The image capturing unit 300 can be a retinal optical tomographic scanner, which is configured to capture a target optical coherence tomographic image of a subject.

The processor 400 is electrically connected to the image capturing unit 300 and stores a program, wherein the program detects a retinal layer thickness and a retinal layer area of the subject when the program is executed by the processor 400. The program includes the target image pre-processing module 410, a retinal layer auto-segmentation model 420, a target image enhancement module 430, the layer thickness detection module 440 and the layer area detection module 450.

The target image pre-processing module 410 is configured to screen and mark the target optical coherence tomographic image, so as to obtain a marked target image. In FIG. 3B, the target image pre-processing module 410 can include a target image quality screening unit 411, a target image scale bar extracting unit 412 and a target image determining unit 413. The target image quality screening unit 411 is configured to screen an image quality of the target optical coherence tomographic image, so as to determine whether the target optical coherence tomographic image meets the image quality. The criteria for determining the image quality are the same as in Step 121. The target image scale bar extracting unit 412 is configured to extract a length of a scale bar of the target optical coherence tomographic image. The target image determining unit 413 is configured to determine a position of an optic nerve of a retina in the target optical coherence tomographic image. For example, when the upper right corner of the target optical coherence tomographic image is displayed as "OD" for the right eye, and "OS" for the left eye.

The retinal layer auto-segmentation model 420 is established by the aforementioned establishing method of the retinal layer auto-segmentation model 100, and the retinal layer auto-segmentation model 420 is used to output the marked target image as a label target image.

The target image enhancement module 430 is configured to perform image enhancement on the label target image to obtain an enhanced label target image.

The layer thickness detection module 440 is configured to calculate the retinal layer thickness in the enhanced label target image, wherein the retinal layer thickness includes retinal layer each region thicknesses. In addition, in FIG. 3C, the layer thickness detection module 440 can include a dividing unit 441, a marking unit 442 and a thickness calculating unit 443. The dividing unit 441 is configured to divide the enhanced label target image into a plurality of retinal layer thickness measurement positions, so as to output a retinal layer each region target image. The marking unit 442 is configured to perform an edge detection analysis and mark lines on the retinal layer each region target image, so as to output a retinal layer each region marked target image. The thickness calculating unit 443 is configured to calculate the retinal layer each region thicknesses in the retinal layer each region marked target image with the length of the scale bar extracted from the target image scale bar extracting unit 412.

The layer area detection module 450 is configured to calculate the retinal layer area in the enhanced label target image, wherein the retinal layer area includes a horizontal retinal layer area and a vertical retinal layer area. In FIG. 3D, the layer area detection module 450 can include a segmenting unit 451 and an area calculating unit 452. The segmenting unit 451 is configured to perform a horizontal retinal segmentation and a vertical retinal segmentation on the enhanced label target image to output a horizontal retinal layer target image and a vertical retinal layer target image. The area calculating unit 452 is configured to calculate the horizontal retinal layer area in the horizontal retinal layer target image and the vertical retinal layer area in the vertical retinal layer target image with the length of the scale bar extracted from the target image scale bar extracting unit 412.

III. Method for Detecting Retinal Layer Thickness and Retinal Layer Area

Figure 4A:
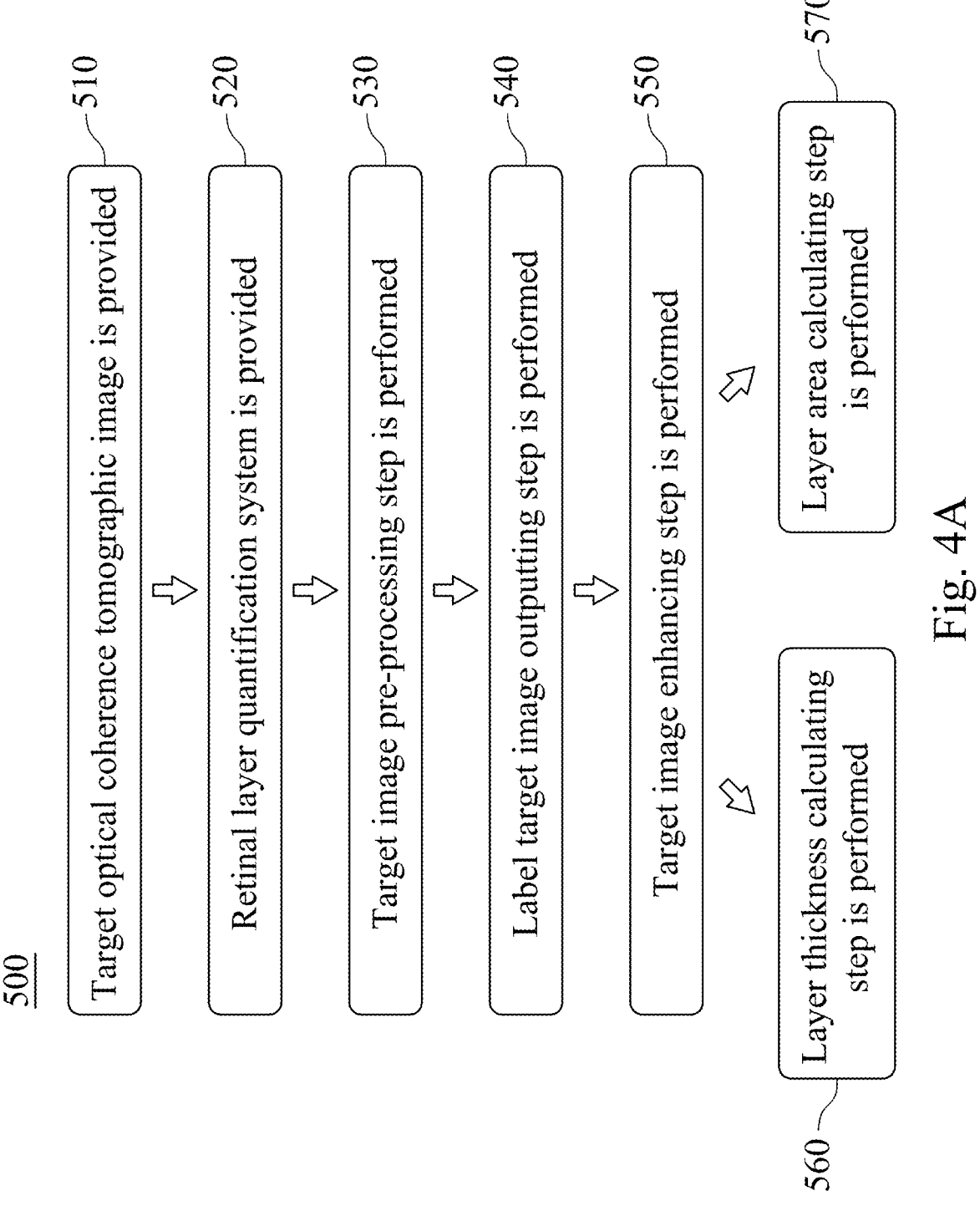
FIG. 4A is a step flow chart of a method for detecting retinal layer thickness and retinal layer area according to still another embodiment of the present disclosure.

Reference is made to FIG. 4A, which is a step flow chart of a method for detecting retinal layer thickness and retinal layer area 500 according to still another embodiment of the present disclosure. The method for detecting retinal layer thickness and retinal layer area 500 includes Step 510, Step 520, Step 530, Step 540, Step 550, Step 560 and Step 570.

In Step 510, a target optical coherence tomographic image of a subject is provided. In Step 520, the retinal layer quantification system 200 is provided.

Figures 4B, 4C:
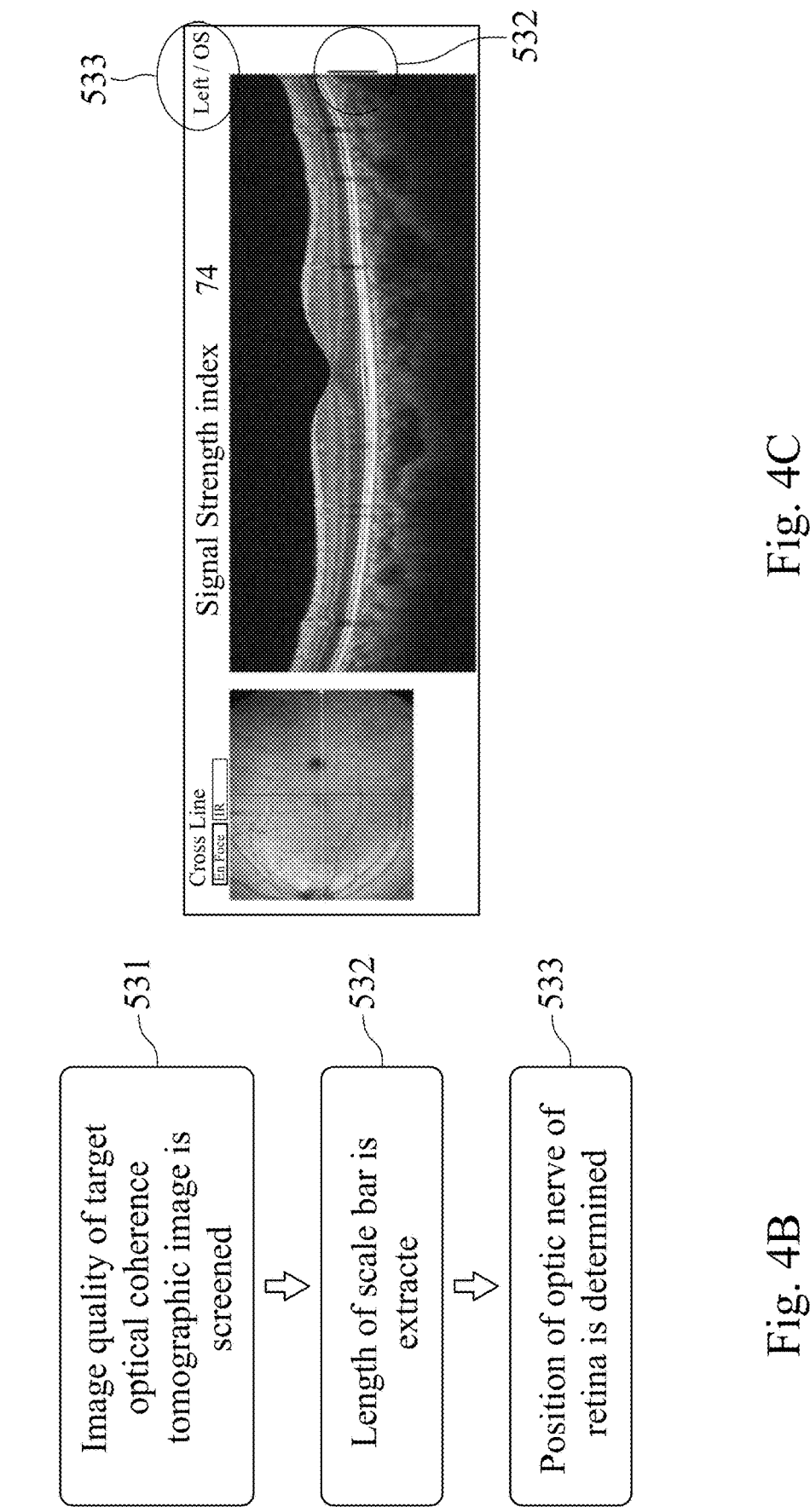
FIG. 4B is a flow chart of Step 530 in FIG. 4A.
FIG. 4C is a schematic diagram of Step 532 and Step 533 in FIG. 4B.

In Step 530, a target image pre-processing step is performed. The target optical coherence tomographic image is screened and marked using the target image pre-processing module 410, so as to obtain the marked target image. Reference is made to FIG. 4B and FIG. 4C. FIG. 4B is a flow chart of Step 530 in FIG. 4A, and Step 530 can further include Step 531, Step 532 and Step 533. FIG. 4C is a schematic diagram of Step 532 and Step 533 in FIG. 4B.

In Step 531, an image quality of the target optical coherence tomographic image is screened using the target image quality screening unit 411, so as to determine whether the target optical coherence tomographic image meets the image quality.

In Step 532, a length of a scale bar of the target optical coherence tomographic image is extracted using a target image scale bar extracting unit 412. In greater detail, the target image scale bar extracting unit 412 extracts a pixel length of the scale bar of the target optical coherence tomographic image, and converts the relationship between the pixel length and the actual length, that is, the length represented by a unit pixel ($\mu$m/pixel).

In Step 533, a position of an optic nerve of a retina in the target optical coherence tomographic image is determined using the target image determining unit 413. FIG. 4C shows the target optical coherence tomographic image for the left eye as an example.

In Step 540, a label target image outputting step is performed. The marked target image is outputted as the label target image using the retinal layer auto-segmentation model 420.

In Step 550, a target image enhancing step is performed. The label target image is processed in an image enhancement method using the target image enhancement module 430, so as to obtain the enhanced label target image. The image enhancement method can include using an anti-Gaussian blur to sharpen the image, and using an image erosion and an image dilation to remove noise points in the image.

Figures 4D, 4E:
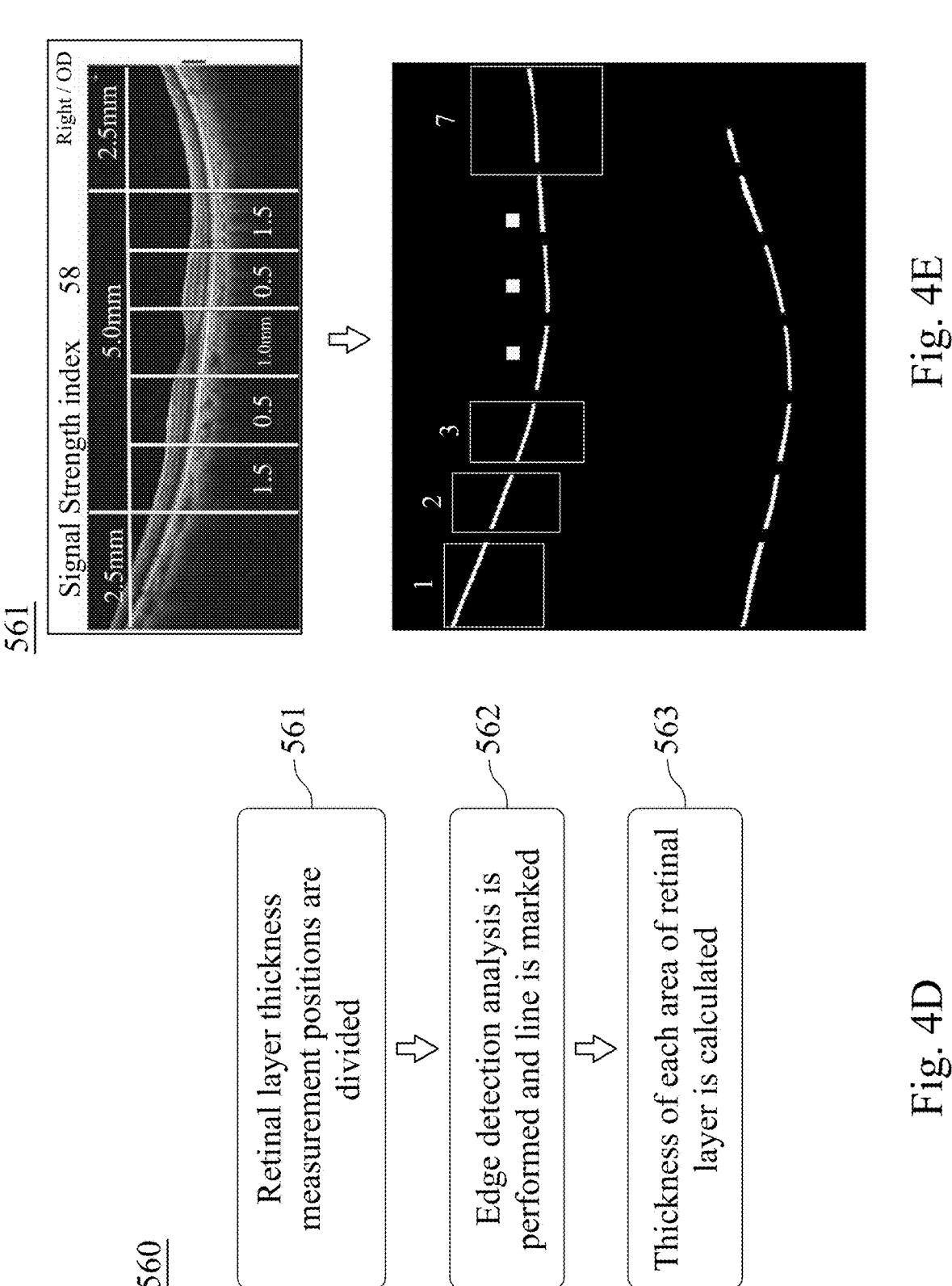
FIG. 4D is a flow chart of Step 560 in FIG. 4A.
FIG. 4E and FIG. 4F show a schematic diagram of Step 561 and Step 563 in FIG. 4D, respectively.
Figure 4G:
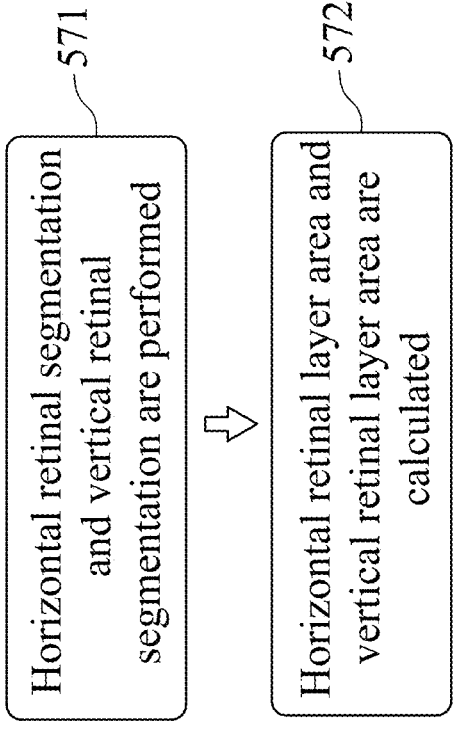
FIG. 4G is a flow chart of Step 570 in FIG. 4A.
Figure 4F:
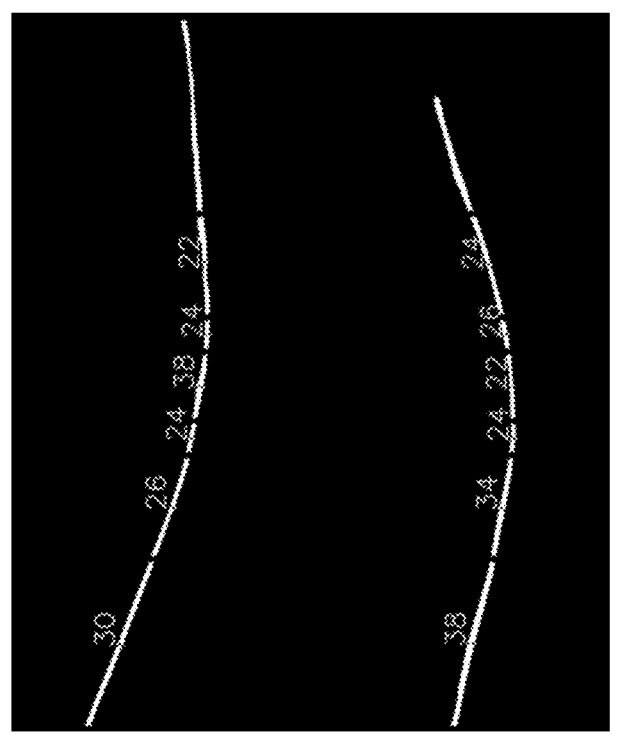

In Step 560, a layer thickness calculating step is performed. The retinal layer each region thicknesses in the enhanced label target image are calculated using the layer thickness detection module 440. Reference is made to FIG. 4D to FIG. 4F. FIG. 4D is a flow chart of Step 560 in FIG. 4A, and Step 560 can further include Step 561, Step 562 and Step 563. FIG. 4E and FIG. 4F show a schematic diagram of Step 561 and Step 563 in FIG. 4D, respectively.

In Step 561, the enhanced label target image is divided into a plurality of retinal layer thickness measurement positions using the dividing unit 441, so as to output a retinal layer each region target image. As shown in FIG. 4E, the dividing unit 441 divides the enhanced label target image into 7 regions, which are the leftmost 2.5 mm region and rightmost 2.5 mm region respectively, and further subdivides the middle 5.0 mm region into 5 regions.

In Step 562, an edge detection analysis is performed and lines are marked on the retinal layer each region target image using the marking unit 442, so as to output a retinal layer each region marked target image. In greater detail, the marking unit 442 performs the edge detection analysis on the retinal layer each region target image to obtain the smallest circumscribed rectangle of each area and finds the midpoint of the rectangle, and then marks the upper and lower points of the midpoint to output the retinal layer each region marked target image.

In Step 563, the retinal layer each region thicknesses in the retinal layer each region marked target image is calculated using the thickness calculating unit 443 with the length of the scale bar extracted from the target image scale bar extracting unit 412. The calculation result is shown in FIG. 4F.

Figures 4H, 4I:
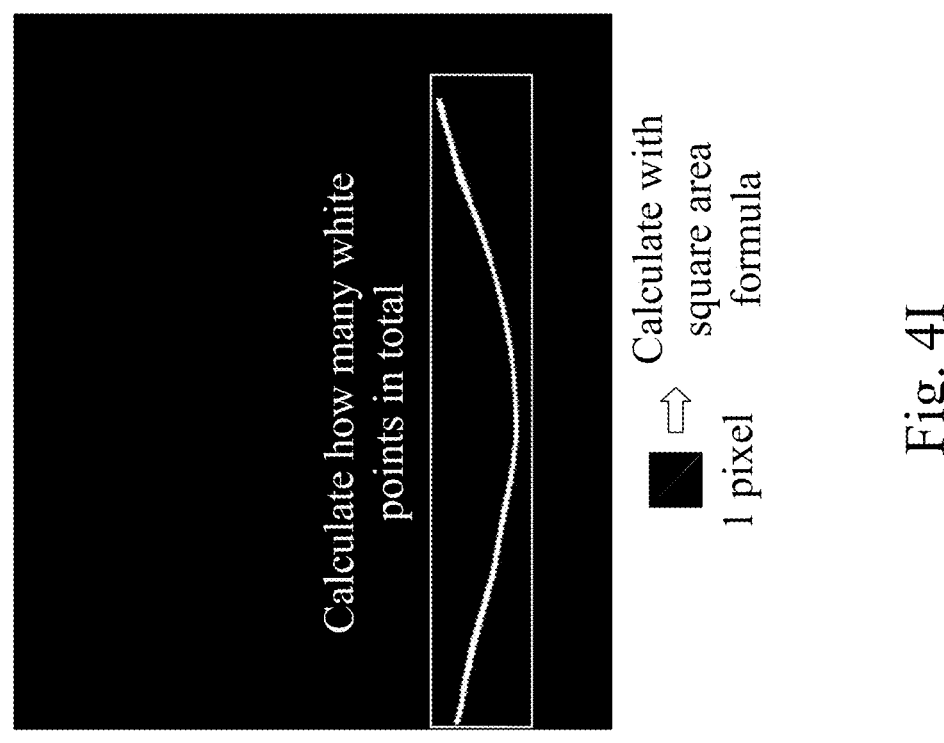
FIG. 4H and FIG. 4I show a schematic diagram of Step 571 and Step 572 in FIG. 4G, respectively.

In Step 570, a layer area calculating step is performed. The horizontal retinal layer area and the vertical retinal layer area in the enhanced label target image are calculated using the layer area detection module 450. Reference is made to FIG. 4G to FIG. 4I. FIG. 4G is a flow chart of Step 570 in FIG. 4A, and Step 570 can further include Step 571 and Step 572. FIG. 4H and FIG. 4I show a schematic diagram of Step 571 and Step 572 in FIG. 4G, respectively.

In Step 571, a horizontal retinal segmentation and a vertical retinal segmentation on the enhanced label target image is performed using the segmenting unit 451, so as to output a horizontal retinal layer target image and a vertical retinal layer target image, as shown in FIG. 4H.

In Step 572, the horizontal retinal layer area in the horizontal retinal layer target image and the vertical retinal layer area in the vertical retinal layer target image are calculated using the area calculating unit 452 with the length of the scale bar extracted from the target image scale bar extracting unit 412. As shown in FIG. 4I, the total amounts of white dots in the framed area are calculated, and then the square area formula and the actual length of the scale bar are applied to calculate the actual area.

IV. Method for Assessing and Predicting Neurodegenerative Disease

Reference is made to FIG. 5, which is a step flow chart of a method for assessing and predicting neurodegenerative disease 600 according to further another embodiment of the present disclosure. The method for assessing and predicting neurodegenerative disease 600 includes Step 610, Step 620, Step 630, Step 640, Step 650, Step 660, Step 670 and Step 680.

In Step 610, a target optical coherence tomographic image of a subject is provided. In Step 620, the retinal layer quantification system 200 is provided.

In Step 630, a target image pre-processing step is performed. The target optical coherence tomographic image is screened and marked using the target image pre-processing module 410, so as to obtain the marked target image. Other technical details are the same as Step 530, and will not be repeated here.

In Step 640, a label target image outputting step is performed. The marked target image is outputted as the label target image using the retinal layer auto-segmentation model 420.

In Step 650, a target image enhancing step is performed. The label target image is processed in an image enhancement method using the target image enhancement module 430, so as to obtain the enhanced label target image. Other technical details are the same as Step 550, and will not be repeated here.

In Step 660, a calculating step is performed. The retinal layer each region thicknesses in the enhanced label target image are calculated using the layer thickness detection module 440, and the horizontal retinal layer area and the vertical retinal layer area in the enhanced label target image are calculated using the layer area detection module 450. Other technical details are the same as Step 560 and Step 570, and will not be repeated here.

In Step 670, a clinical test data of the subject is provided. The clinical test data can include a computed tomography (CT) image, an magnetic resonance imaging (MRI) image, a blood test value, a personal medical history, a family medical history, a past surgery history, a medical evaluation scale, a physiological value and a past medication habit.

In Step 680, the clinical test data is compared with the thickness of each area of retinal layer, the horizontal retinal layer area and the vertical retinal layer area by a regression analysis model, so as to calculate an assessing grade representing a possibility of the subject having neurodegenerative disease.

V. Eye Care device

Figure 6:
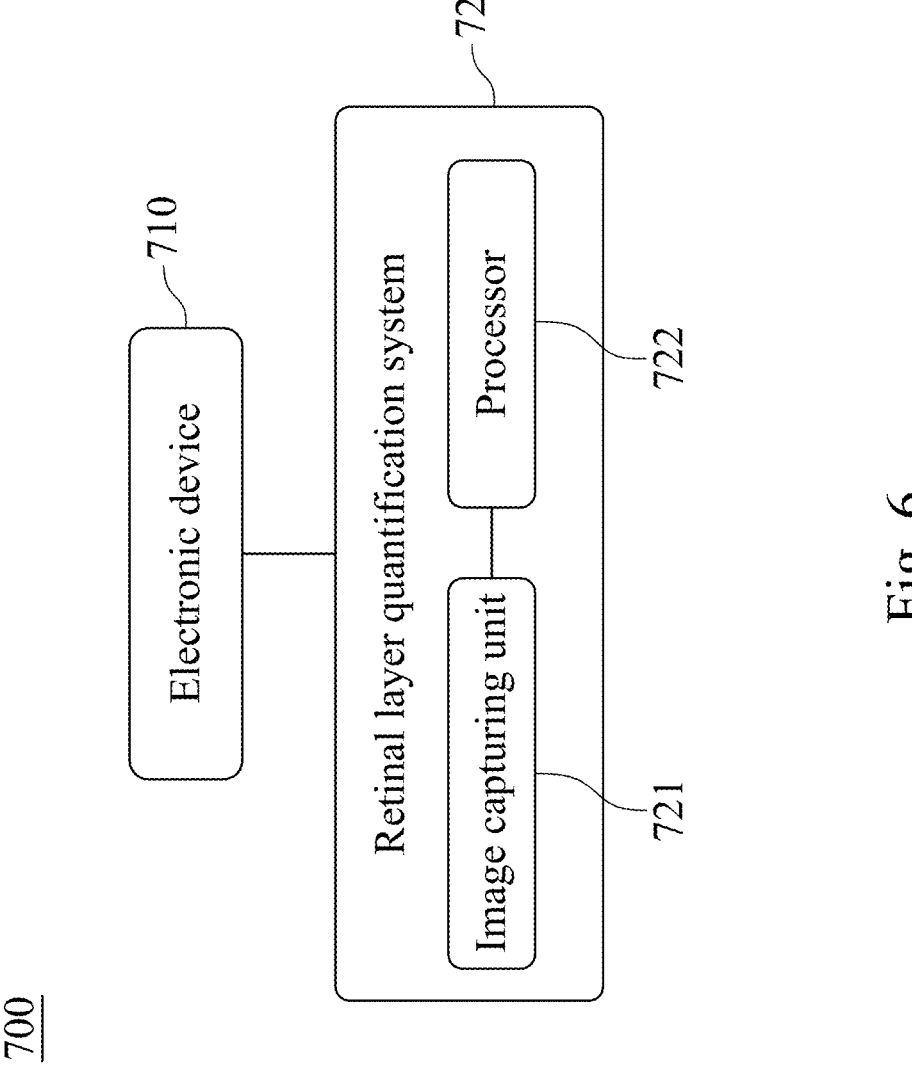
FIG. 6 is a structural schematic view of an eye care device according to one another embodiment of the present disclosure.

Reference is made to FIG. 6, which is a structural schematic view of an eye care device 700 according to one another embodiment of the present disclosure. In FIG. 6, the eye care device 700 includes an electronic device 710 and a retinal layer quantification system 720. The electronic device 710 is connected to the retinal layer quantification system 720 through telecommunication. In detail, the retinal layer quantification system 720 includes an image capturing unit 721 and a processor 722, and is similar to the structure of the retinal layer quantification system 200 in FIG. 3A. The electronic device 710 can further show a retinal layer thickness and a retinal layer area output by the processor 722 of the retinal layer quantification system 720, or further go with an assessing grade representing a possibility of a subject having neurodegenerative disease output by a regression analysis model (not shown). Also, the electronic device 710 can further show an assessing result of the subject having ophthalmic diseases or neurodegenerative disease and follow-up recommended medical plans such as medication or referral in real time.

Furthermore, though it is not shown in the figures, the image capturing unit 721 in the eye care device 700 of the present disclosure can be a retinal optical tomographic scanner, so as to capture a target optical coherence tomographic image of the subject. The electronic device 710 can be a portable electronic device such as a mobile phone or a tablet. The processor 722 can further be integrated into the electronic device, which makes the processor 722 not only easy to carry, but also beneficial to the sensitivity and convenience of subsequent large-scale eye and brain function screening, which the present disclosure is not limited thereto.

VI. Example

1. Reference Database

The reference database used in the present disclosure includes retinal images of normal subjects and subjects with neurodegenerative diseases (mild cognitive impairment, Parkinson's disease, depression, mental illness, multiple sclerosis, muscular dystrophy, lupus erythematosus, phenylketonuria, etc.), and the retinal images are classified into normal group and neurodegenerative disease group based on blood test values, tomographic images, magnetic resonance imaging (MRI) images, and physician diagnosis of the subjects. In this test example, the data set includes a total of 9,500 sample groups, which are further divided into 7,500 training sample groups as the training set, 1,500 validation sample groups as the validation set, and 500 test sample groups. Each of the sample groups includes a reference optical coherence tomographic image, a control label image, an adjusted reference optical coherence tomographic image, and an adjusted control label image.

Figure 7A:
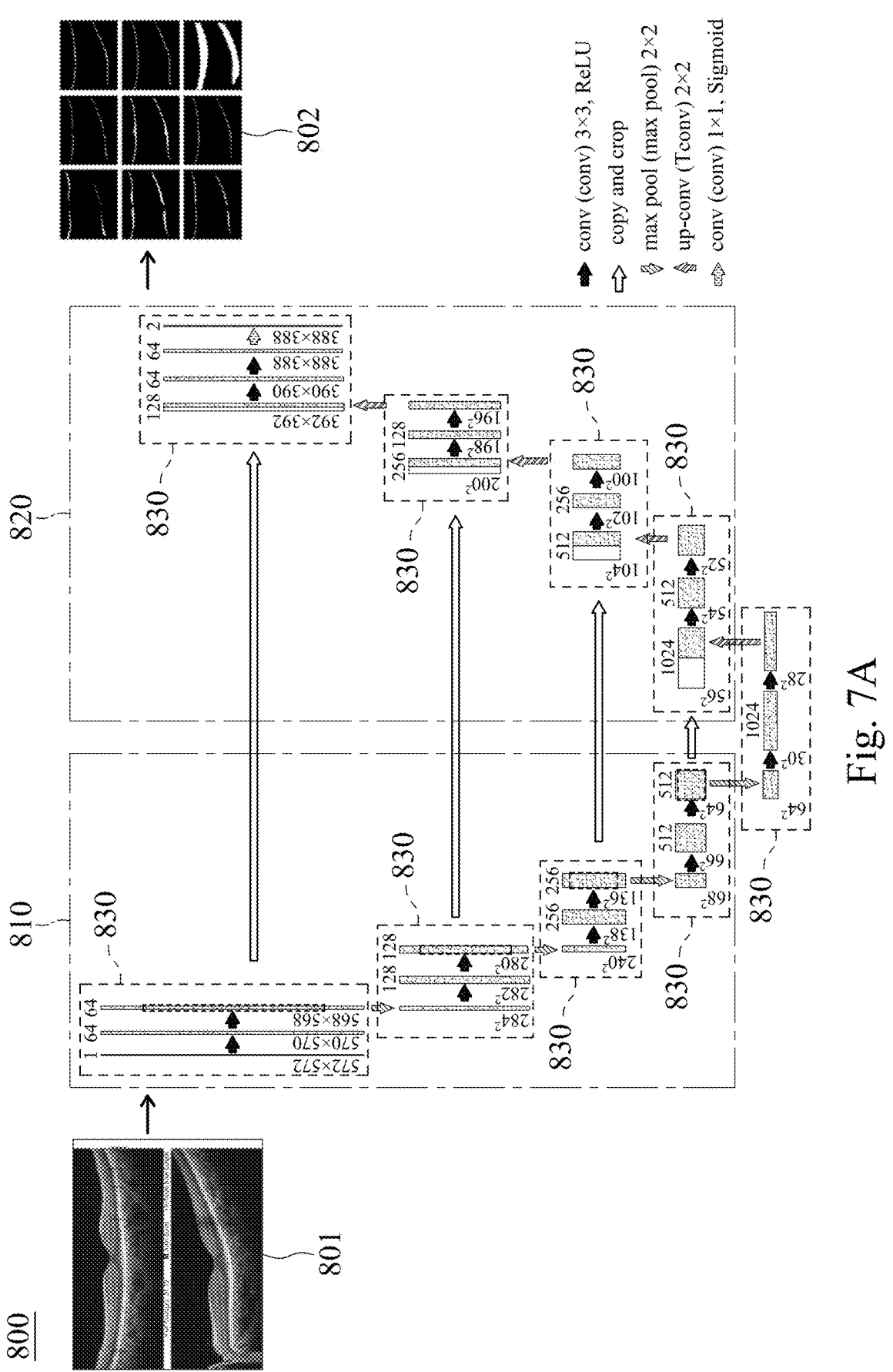
FIG. 7A is a structural schematic view of a U-net convolution neural network learning classifier according to the present disclosure.

2. U-net Convolution Neural Network Learning Classifier According to the Present Disclosure Reference is made to FIG. 7A, which is a structural schematic view of a U-net convolution neural network learning classifier 800 according to the present disclosure. In FIG. 7A, the U-net convolution neural network learning classifier 800 is mainly composed of an encoder 810 and a decoder 820, and the encoder 810 and the decoder 820 are connected to each other by a skip connection. The U-net convolution neural network learning classifier 800 includes 9 sampling modules 830, wherein the encoder 810 includes 4 sampling modules 830, and the decoder 820 includes 4 sampling modules 830. The encoder 810 is the contracting path for capturing contextual information with 4 times downsampling. The decoder 820 is the expanding path for fine positioning to restore image size with 4 times upsampling. After the outputted each layer control label image feature values of each layer of the encoder 810 are copied and cropped, they are fused with the corresponding transpose convoluted each layer control label image feature values in the decoder 820, and then used as the input of the next layer to perform follow-up upsampling. After inputting the reference optical coherence tomographic image 801, it is executed by the encoder 810. In the encoder 810, a pooling method (Pool) is used between every two sampling modules 830 to reduce image size, extract image features, and improve neuron field of view. In the decoder 820, a transpose convolution method (TConv) is used between every two sampling modules 830 to gradually enlarge the image size. In the U-net convolution neural network learning classifier 800 of the present disclosure, the output of each sampling module 830 in the encoder 810 is connected to the input of the sampling module 830 in the decoder 820 corresponding, thereby the features obtained at different levels are retained, and finally the label reference image 802 is outputted. The obtained label reference image 802 can be compared with the control label image to confirm the accuracy of the retinal layer auto-segmentation model of the present disclosure.

Figure 7B:
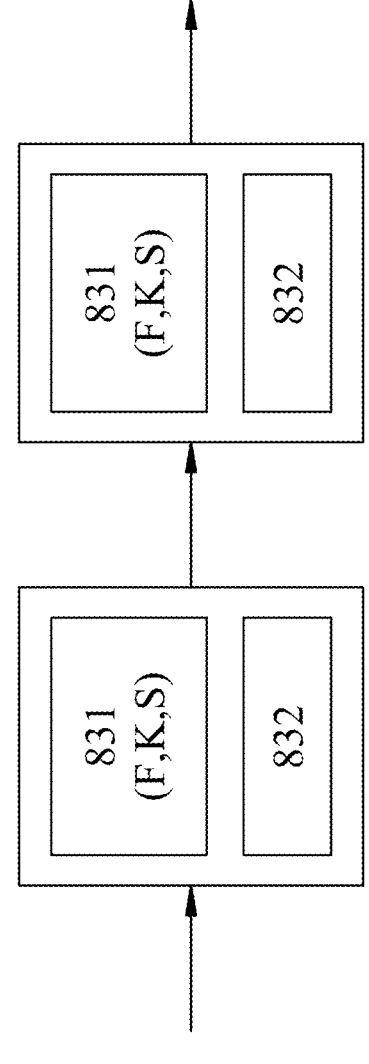
FIG. 7B is a structural schematic view of a sampling module in FIG. 7A.

Reference is made to FIG. 7B, which is a structural schematic view of a sampling module 830 in FIG. 7A. The sampling module 830 can include a convolutional layer 831 and a nonlinear activation layer 832. The output feature of each of the sampling module 830 uses a padding method to maintain the image size of the sampling module 830 entirely, that is, the image size remains unchanged after the image is calculated by each sampling module 830, only the channel size changes. In FIG. 7B, F represents filters, K represents kernel size, and S represents strides.

The activation function used in the U-net convolution neural network learning classifier 800 is the nonlinear activation layer 832. Compared with other neural network activation functions, the nonlinear activation layer 832 has the advantages of neural network sparsity, more efficient increase of neural network nonlinearity and backpropagation, prevention of gradient disappearance, and simplified operation process.

The loss function used in the U-net convolution neural network learning classifier 800 of the present disclosure is shown as Formula (1), which has the main function of calculating the similarity between the evaluation training result of the deep learning network and the target result.

$$DiceCoefficient\_loss = \left(1 - 2 * \frac{|X| \cap |Y|}{|X| + |Y|}\right). \qquad \text{Formula (1)}$$

The network parameters $W_{l+1}$ of the U-net convolution neural network learning classifier 800 of the present disclosure are updated recursively by using the Mini Batch Gradient Descent with Moment Estimation technology as shown in Formula (2).

$$w_{l+1} = w_l - \frac{\eta m^l}{\sqrt{v_l} + \epsilon}. \qquad \text{Formula (2)}$$

In Formula (2), $\eta$ is the learning rate, and $\epsilon$ is a constant with a small value, which is mainly used to avoid the phenomenon that the denominator of the second item in Formula (2) from being zero. When updating the network parameters, the U-net convolution neural network learning classifier 800 of the present disclosure considers mini batches with the amount of B. Therefore, there are averages of the first-order gradient descent method and the second-order gradient descent method in Formula (3) and Formula (4) and an average amount thereof is the amount of B of the mini batches. Furthermore, $\beta_1$ and $\beta_2$ are decay rates. The method of the U-net convolution neural network learning classifier 800 randomly choosing the sample groups with the amount of B from the testing sample groups for deep learning every time is called mini batches.

$$m_l = \beta_1 m_{l-1} + (1 - \beta_1) \frac{1}{B} \Sigma_{x_r \in B}^B \nabla L^r(w^l); \qquad \text{Formula (3)}$$

$$v_l = \beta_2 v_{l-1} + (1 - \beta_2) \frac{1}{B} \Sigma_{x_r \in B}^B [\nabla L^r(w^l)]^2 \qquad \text{Formula (4)}$$

US 12,661,001 B2

13

3. Training Steps

The training set and the validation set are putted into the U-net convolution neural network learning classifier 800 of the present disclosure for training. According to the training results of each batch, if the target with Loss less than 3% cannot be achieved, the neural network parameter adjustment program will be updated to retrain until the target is achieved. In greater detail, the adjustable related parameters include activation function, learning rate, normalization factor, decay rate, number of neurons per layer, number of neuron levels, batch size, order of magnitude, training sample group and validation sample group. During training, the training results and parameter adjustments are continuously monitored until the condition is improved.

When the training result satisfies that the Loss is less than 3% and no overfitting occurs to achieve convergence, the retinal layer auto-segmentation model of the present disclosure is obtained. A plurality of label reference images are outputted using the retinal layer auto-segmentation model, and each of the plurality of label reference images is compared with corresponding one of the plurality of control label images, so as to confirm an accuracy of the retinal layer auto-segmentation model.

Figure 8A:
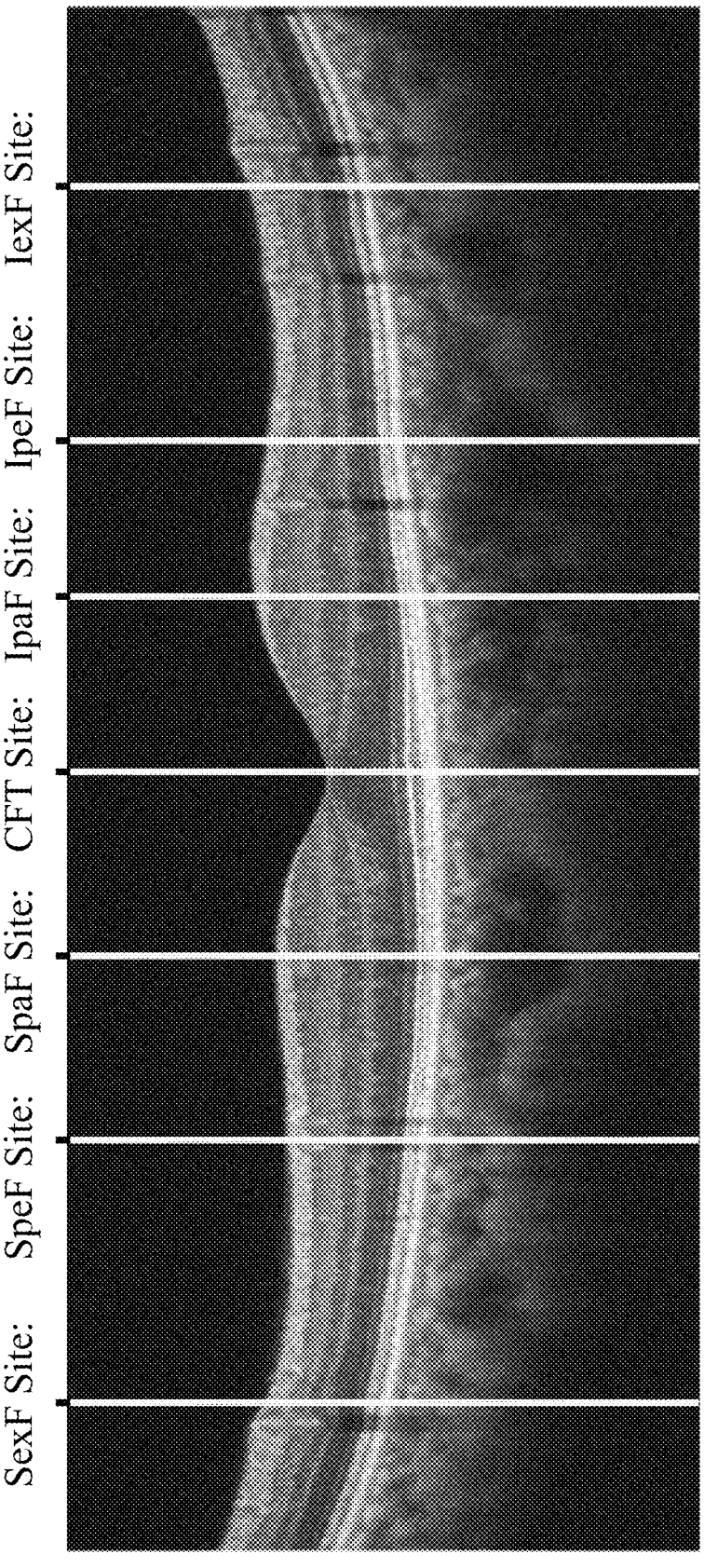
FIG. 8A is a schematic diagram showing retinal layer thickness measurement positions.
Figure 8B:
FIG. 8B shows an output result after measuring thicknesses and areas of each of retinal layers.
Figure 8C:
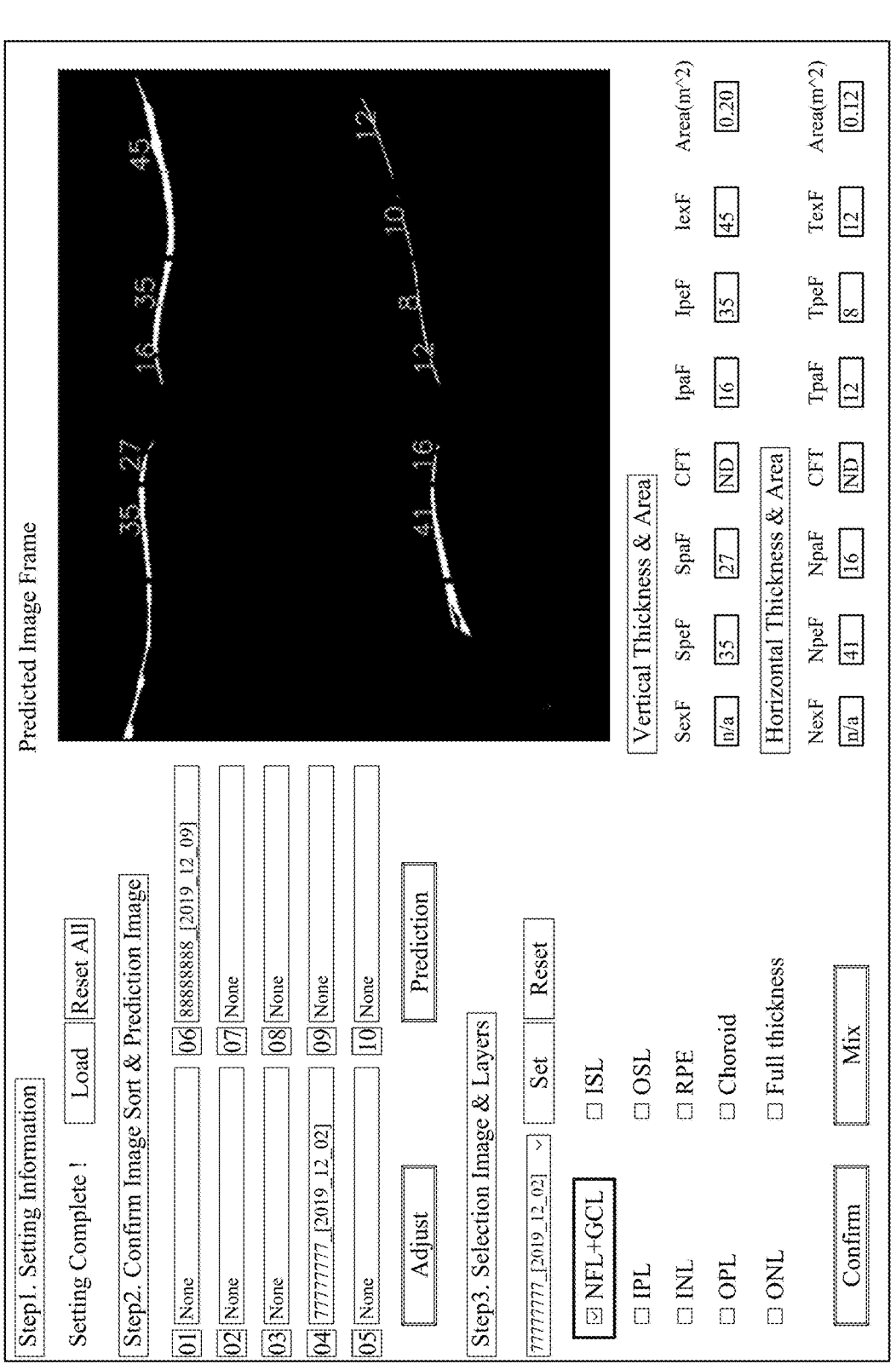
FIG. 8C shows an output result after measuring a thickness and an area of retinal monolayer.

4. Measurement of the Retinal Layer Thickness and Measurement of the Retinal Layer Area The retinal layer quantitative system of the present disclosure is further tested to detect the retinal layer thickness and retinal layer area of the subject. The target optical coherence tomography image of the subject is performed with the method for detecting retinal layer thickness and retinal layer area 500. Reference is made to FIG. 8A to FIG. 8C. FIG. 8A is a schematic diagram showing retinal layer thickness measurement positions. FIG. 8B shows an output result after measuring thicknesses and areas of each of retinal layers. FIG. 8C shows an output result after measuring a thickness and an area of retinal monolayer. In FIG. 8A to FIG. 8C, in the abbreviations of SexF, SpeF, SpaF, CFT, IpaF, IpeF, lexF, TexF, TpeF, TpaF, NexF, NpeF and NpaF, S represents Superior, I represents Inferior, N represents Nasal, T represents Temporal, CFT represents Central Foveal Thickness, exF represents Extra Fovea, peF represents Peri Fovea, paF represents Para Fovea.

The enhanced label target image outputted by the target image enhancement module in the retinal layer quantitative system of the present disclosure can use the dividing unit and the marking unit to output the retinal layer each region marked target image (as shown in FIG. 8A). Then the retinal layer each region thicknesses in the enhanced label target image are calculated using the layer thickness detection module. For example, the thickness calculating unit of the layer thickness detection module reads one of the retinal layer each region marked target images marked by the dividing unit and the marking unit from the folder each time, and saves the result of the retinal layer each region thicknesses into Excel. The Excel data is arranged according to different medical record numbers and examination dates, and the calculation of the retinal layer each region thicknesses of all enhanced label target images in the folder is automatically completed. In addition, the enhanced label target image outputted by the target image enhancement module in the retinal layer quantitative system of the present disclosure can also use the segmenting unit to output the horizontal retinal layer target image and the vertical retinal layer target image. Then the horizontal retinal layer area and the vertical retinal layer area of the enhanced label target image are calculated using the area calculating unit of the layer area detection module. For example, the area calculating unit of the layer area detection module reads two of the horizontal retinal layer target image and the vertical retinal layer target image segmented by the segmenting unit from the folder each time, calculates the horizontal retinal layer area and the vertical retinal layer area with the length of the scale bar extracted from the target image scale bar extracting unit, and saves the calculation result into Excel. The Excel data is arranged according to different medical record numbers and examination dates, and the calculation of the horizontal retinal layer area and the vertical retinal layer area of all enhanced label target images in the folder is automatically completed. Therefore, the retinal layer quantitative system of the present disclosure can improve the problems caused by relying on human intervention, and can be integrated with various electronic devices and equipment to improve the overall detection efficiency and accuracy. As shown in FIG. 8B and FIG. 8C, relevant personnel can query the retinal layer thickness and retinal layer area of each of retinal layers and retinal monolayer.

5. Correlation of the Retinal Layer Thickness and the Retinal Layer Area with Neurodegenerative Diseases Due to the same origin of the retina and the central nervous system, previous studies have shown that changes in the thickness of the choroid layer are highly correlated with mild Alzheimer's disease, essential tremors, and epilepsy. For example, changes in the retinal pigment epithelium (RPE) thickness are associated with metabolic syndrome, white matter leukoplakia, and schizophrenia; changes in the outer nuclear layer (ONL) are associated with Parkinson's disease, Alzheimer's disease, and albinism; thinning of outer plexiform layer (OPL) is associated with Parkinson's disease, multiple sclerosis, and Niemann-Pick type C; changes in the inner nuclear layer (INL) are associated with phenylketonuria and multiple sclerosis; changes in the inner plexiform layer (IPL) are associated with bipolar disorder, Parkinson's disease, relapsing multiple sclerosis, changes in gray and white matter volume, essential tremors, and epilepsy; and changes in the ganglion cell layer (GCL) and nerve fiber layer (NFL) are associated with Alzheimer's disease, depression, schizophrenia, multiple sclerosis, Parkinson's disease, muscle Atrophic lateral sclerosis and lupus erythematosus. The aforementioned studies have shown that thickness of each of retinal layers are closely related to neurodegenerative diseases.

The present disclosure further utilizes a regression analysis model to compare the thickness of each area of retinal layer, the horizontal retinal layer area or the vertical retinal layer area calculated by the retinal layer quantitative system of the present disclosure with the clinical test data, such as the CT image, the MRI image and the blood test value, to calculate the assessing grade representing the possibility of the subject having neurodegenerative disease. Further, a system based on the optical coherence tomographic images can be established to warn and predict whether a subject is suffering from a neurodegenerative disease by detecting the retinal layer thickness and retinal layer area of each of retinal layers and retinal monolayer. Therefore, the purpose of assessing and predicting neurodegenerative disease in advance based on the optical coherence tomographic image and the clinical test data can be achieved.

Figure 9:
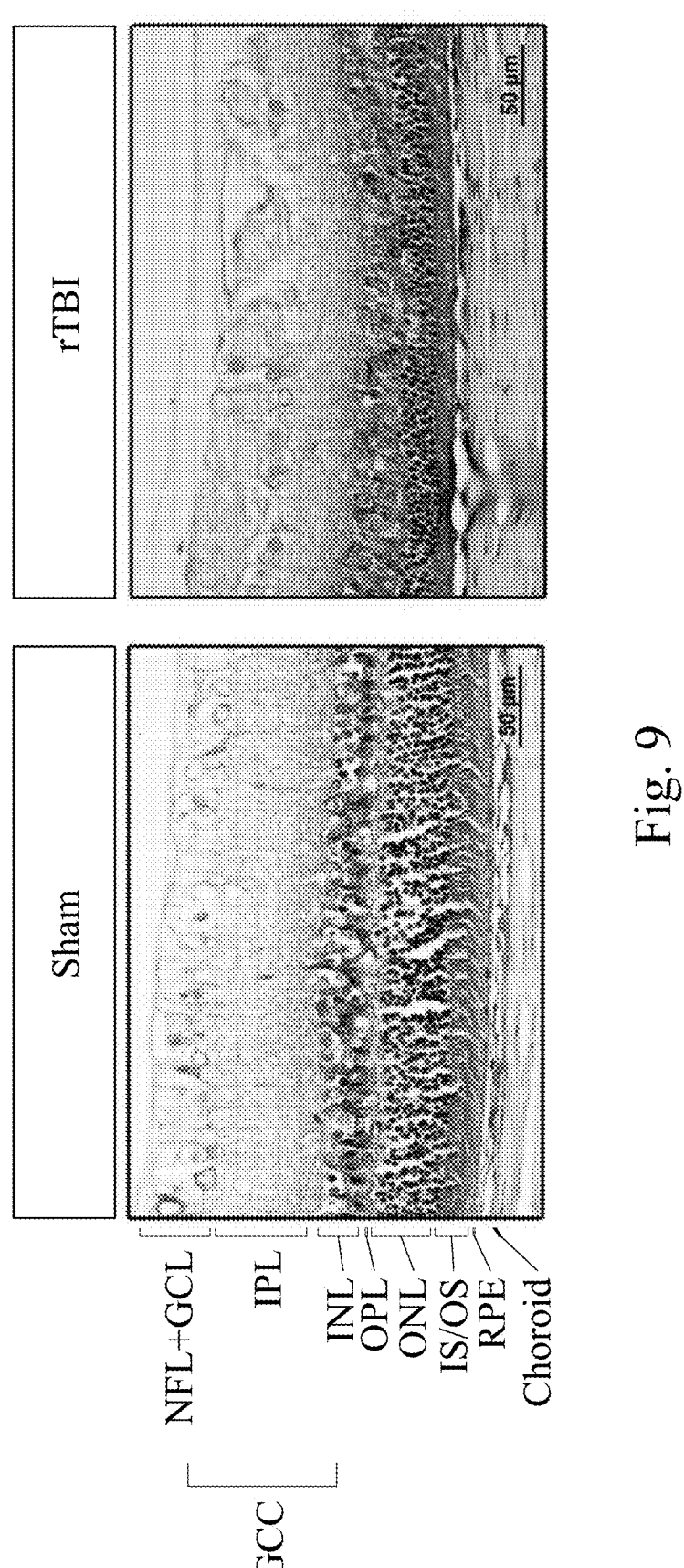
FIG. 9 shows analysis results of cell thicknesses of each of retinal layers in the experimental animals.
Figure 10:
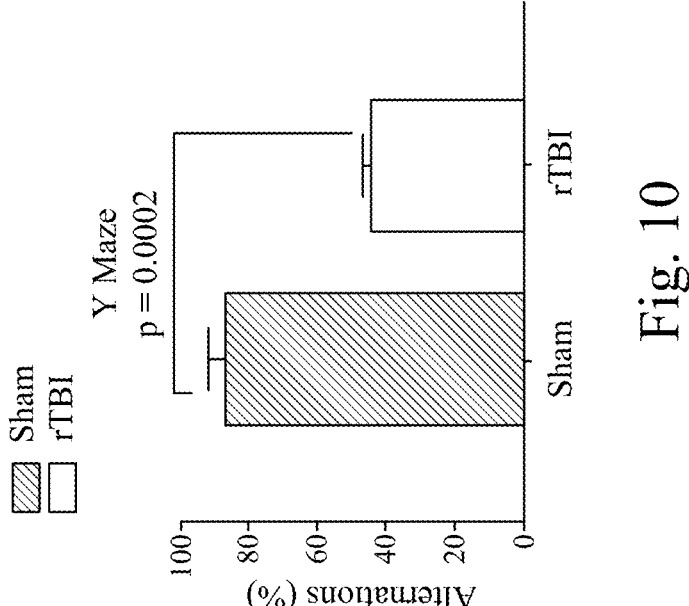
FIG. 10 shows analysis results of cognitive function performance in the Y maze test of the experimental animals.
Figure 11B:
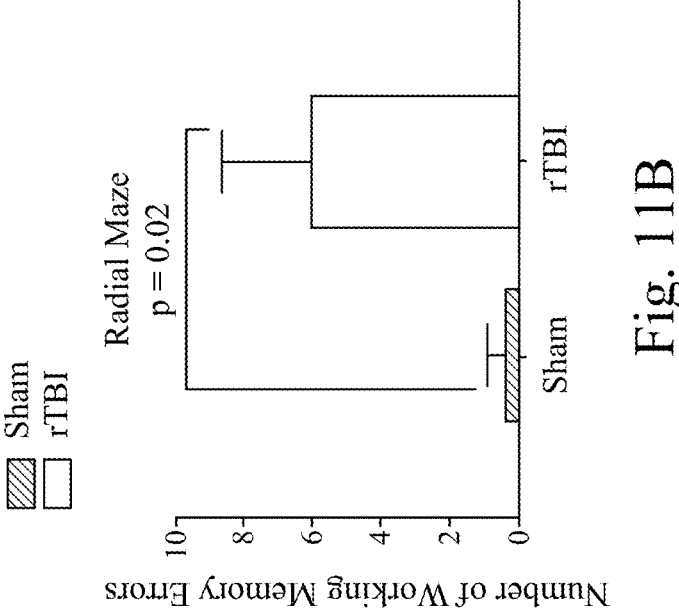
FIG. 11A and FIG. 11B show analysis results of cognitive function performance in the radial maze test of the experimental animals.
Figure 11A:
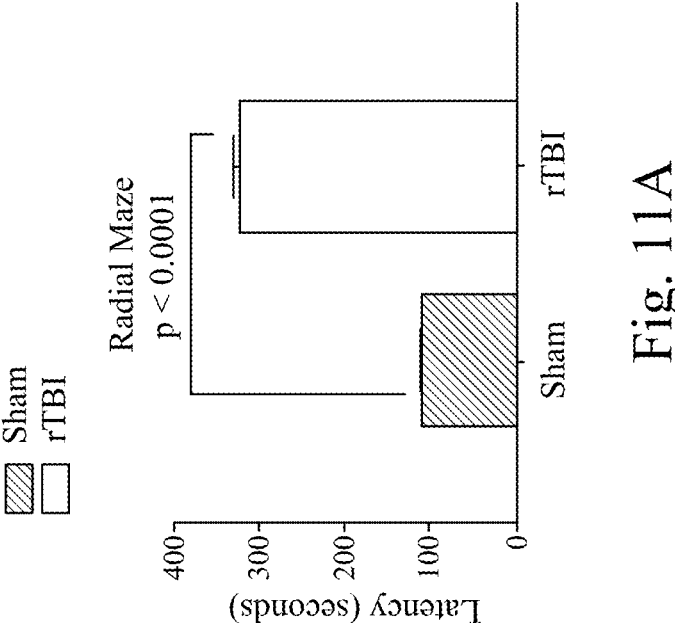
Figures 12A, 12B, 12C, 12D, 12E, 12F:
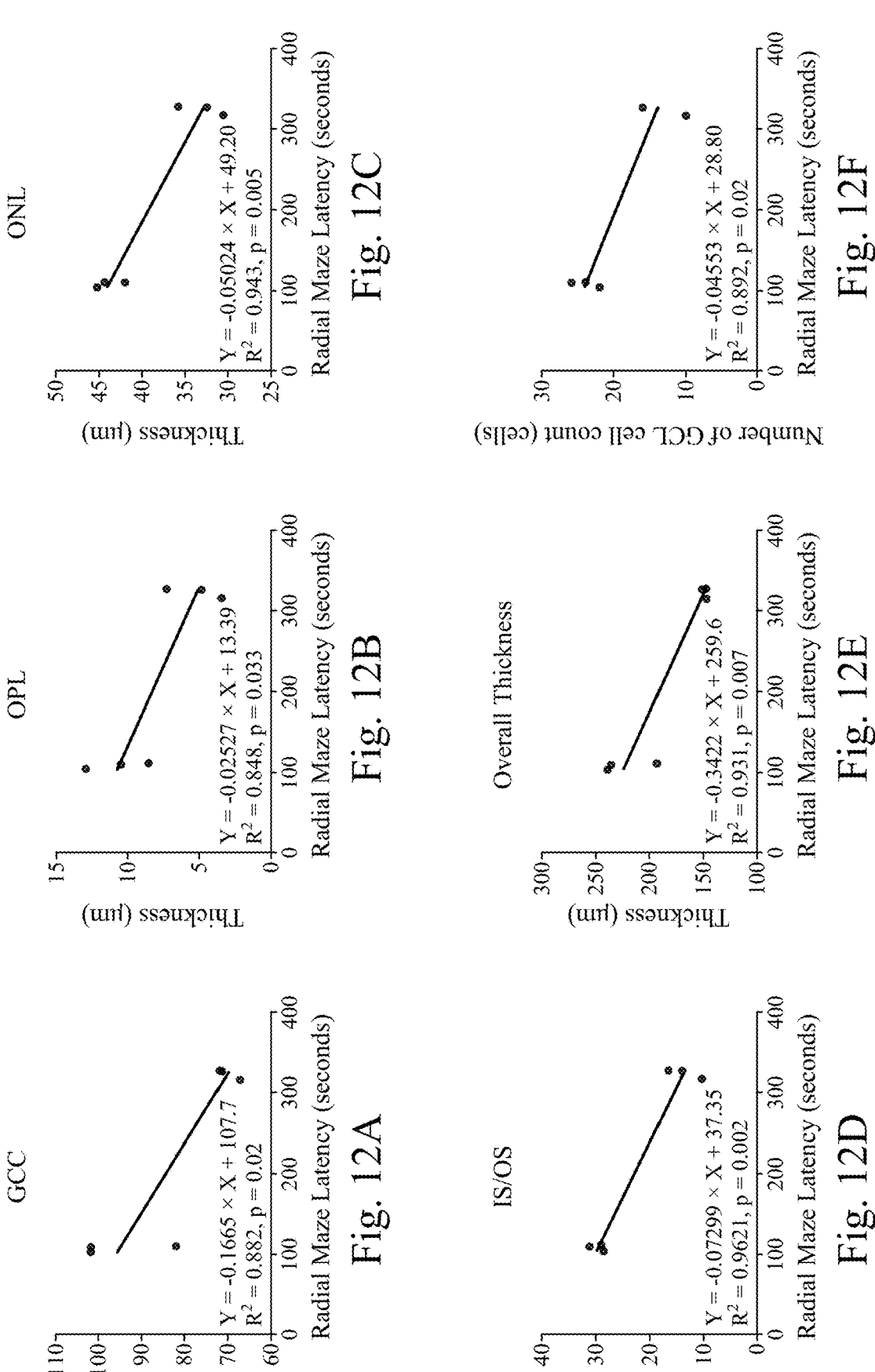
FIG. 12A, FIG. 12B, FIG. 12C, FIG. 12D, FIG. 12E, FIG. 12F, FIG. 13A, FIG. 13B, FIG. 13C, FIG. 13D, FIG. 13E, FIG. 13F, FIG. 14A, FIG. 14B and FIG. 14C show analysis results of the correlation between cognitive function performance in the Y maze test and the radial maze test of the experimental animals and the thickness of each of retinal layer and the number of cells in the ganglion cell layer.
Figures 13A, 13B, 13C, 13D, 13E, 13F:
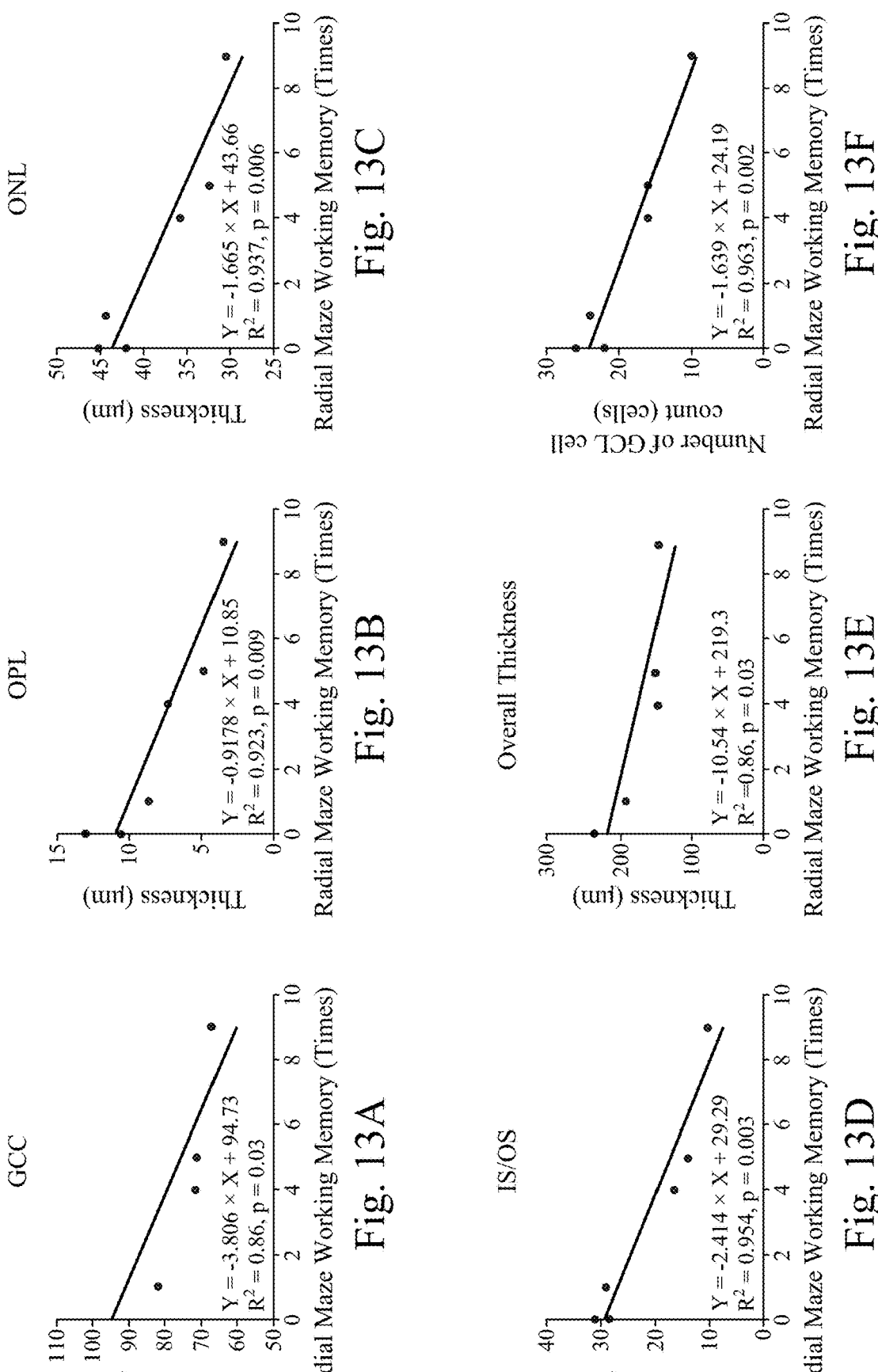

The experimental animals were subjected to repetitive traumatic brain injury (rTBI) to induce traumatic neurodegenerative diseases, and after successful induction, the optical coherence tomographic images of rats with traumatic neurodegenerative diseases were obtained. The cognitive function performance of rats with traumatic neurodegenerative diseases were analyzed by the Y maze test and the radial maze test. Reference is made to FIG. 9 to FIG. 14C. FIG. 9 shows analysis results of cell thicknesses of each of retinal layers in the experimental animals. FIG. 10 shows analysis results of cognitive function performance in the Y maze test of the experimental animals. FIG. 11A and FIG. 11B show analysis results of cognitive function performance in the radial maze test of the experimental animals. FIG. 12A, FIG. 12B, FIG. 12C, FIG. 12D, FIG. 12E, FIG. 12F, FIG. 13A, FIG. 13B, FIG. 13C, FIG. 13D, FIG. 13E, FIG. 13F, FIG. 14A, FIG. 14B and FIG. 14C show analysis results of the correlation between cognitive function performance in the Y maze test and the radial maze test of the experimental animals and the thickness of each of retinal layer and the number of cells in the ganglion cell layer. In FIG. 9 to FIG. 11B, rTBI represents the rats with traumatic neurodegenerative disease, and Sham represents negative control group.

Figure 14C:
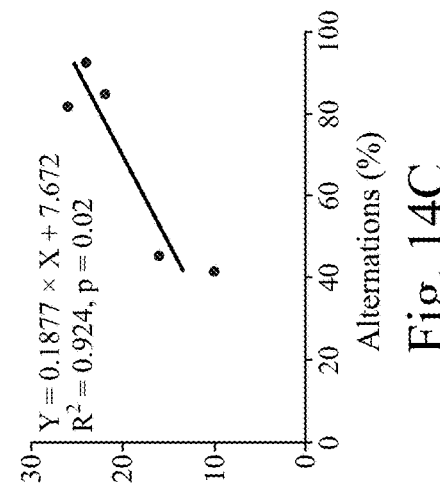
Figure 14B:
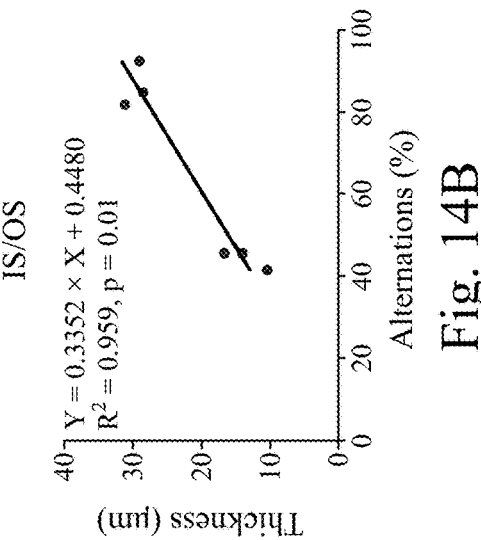
Figure 14A:
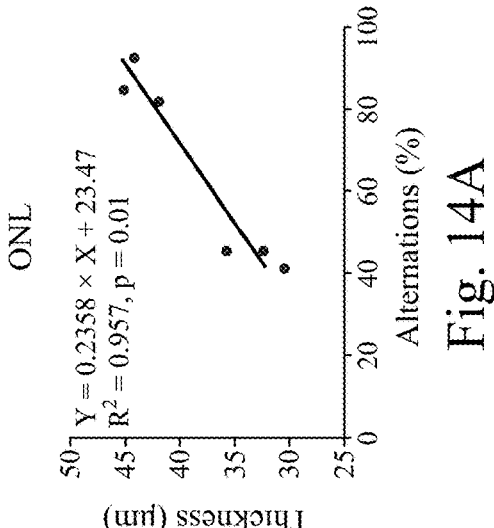

In FIG. 9, the eyeballs of the negative control group and rats with traumatic neurodegenerative disease were stained with hematoxylin-eosin to identify the cytoplasm and nucleus, and the thickness and number of cells in each of retinal layers were analyzed. The results show that the rats with traumatic neurodegenerative disease have significantly thinner retinas. The results in FIG. 10 show that the rats with traumatic neurodegenerative disease have significantly worse cognitive function than negative control group. The results in FIG. 11A show that the rats with traumatic neurodegenerative disease spend significantly more time searching for food than negative control group. The results in FIG. 11B show that number of working memory errors in the rats with traumatic neurodegenerative disease is significantly higher than that in the negative control group, indicating that the rats with traumatic neurodegenerative disease were successfully induced. The results in FIG. 12A to FIG. 13F show that the rats with traumatic neurodegenerative disease using longer search time for food and having the worse the short-term memory ability and spatial memory ability, the thickness of the retinal ganglion cell complex (GCC), the outer plexiform layer (OPL), the outer nuclear layer (ONL), the photoreceptor cell layer (IS/OS) and overall thickness thereof are lower, and the number of cells in the ganglion cell layer (GCL) thereof is lower. The Y maze test is used to test the willingness to explore a new environment and is used to assess the short-term and spatial memory of the experimental animals. The results in FIG. 14A to FIG. 14C show that the thickness of the outer nuclear layer (ONL), the thickness of the photoreceptor cell layer (IS/OS) and the number of ganglion cells are positively correlated with the percentage of spontaneous alternation behavior. That is, the thinner the outer nuclear layer and the photoreceptor cell layer and the fewer the number of ganglion cells in the rats with traumatic neurodegenerative disease, the worse their short-term memories and spatial memories are. The results are consistent with that of FIG. 9, indicating that the retinal layer thickness and the retinal layer area are associated with the neurodegenerative disease. Therefore, the retinal layer quantitative system of the present disclosure can be used together with the regression analysis model for analysis, so that the retinal layer quantitative system of the present disclosure is beneficial to further assess and predict the risk of a subject suffering from neurodegenerative disease.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An establishing method of a retinal layer auto-segmentation model, comprising:

obtaining a reference database, wherein the reference database comprises a plurality of reference optical coherence tomographic images;

performing a reference image pre-processing step to duplicate each of the plurality of reference optical coherence tomographic images, mark a cell segmentation line of each of retinal layers and crop each of the plurality of reference optical coherence tomographic images, so as to obtain a plurality of control label images;

performing an image feature selecting step to analyze each of the plurality of control label images by a feature selecting module, and obtain an each layer control label image feature from each of the plurality of control label images, so as to obtain a plurality of each layer control label image features;

performing a data set generating step to process the reference optical coherence tomographic images and corresponding one of the control label images in a data enhancement method to obtain a data set, and divide the data set into a training set and a validation set, wherein the data set comprises the plurality of reference optical coherence tomographic images, the plurality of control label images, a plurality of adjusted reference optical coherence tomographic images and a plurality of adjusted control label images;

performing a training step to train the training set with the plurality of each layer control label image features through a U-net convolution neural network learning classifier to reach convergence, so as to obtain the retinal layer auto-segmentation model; and performing a confirming step to output a plurality of label reference images from the validation set using the retinal layer auto-segmentation model, and to compare each of the plurality of label reference images with corresponding one of the plurality of control label images, so as to confirm an accuracy of the retinal layer auto-segmentation model;

wherein the data enhancement method comprises an image flip, an image translation, an adjustment of brightness and an adjustment of scale.

2. The establishing method of the retinal layer auto-segmentation model of claim 1, wherein the reference image pre-processing step comprises:

performing an image quality screening on the plurality of reference optical coherence tomographic images, and retaining the plurality of reference optical coherence tomographic images meeting an image quality;

marking the cell segmentation line of each of retinal layers in each of the plurality of reference optical coherence tomographic images, so as to obtain a plurality of marked optical coherence tomographic images; and cropping the plurality of marked optical coherence tomographic images respectively, so as to obtain the plurality of control label images.

3. The establishing method of the retinal layer auto-segmentation model of claim 1, wherein the image feature selecting step comprises:

performing an image layering on each of the plurality of control label images to obtain a plurality of each layer control label images, wherein each of the plurality of each layer control label images comprises 9 retinal monolayer images; and normalizing the plurality of each layer control label images, so as to obtain the plurality of each layer control label image features.

4. The establishing method of the retinal layer auto-segmentation model of claim 1, wherein the U-net convolution neural network learning classifier comprises 4 times of downsampling and 4 times of upsampling.

5. A retinal layer quantification system, comprising:

an image capturing unit configured to capture a target optical coherence tomographic image of a subject; and a processor electrically connected to the image capturing unit and storing a program, wherein the program detects a retinal layer thickness and a retinal layer area of the subject when the program is executed by the processor, and the program comprises:

a target image pre-processing module configured to screen and mark the target optical coherence tomographic image, so as to obtain a marked target image;

a retinal layer auto-segmentation model established by the establishing method of the retinal layer auto-segmentation model of claim 1, and the retinal layer auto-segmentation model is used to output the marked target image as a label target image;

a target image enhancement module configured to perform image enhancement on the label target image to obtain an enhanced label target image;

a layer thickness detection module configured to calculate the retinal layer thickness in the enhanced label target image, wherein the retinal layer thickness comprises retinal layer each region thicknesses; and a layer area detection module configured to calculate the retinal layer area in the enhanced label target image, wherein the retinal layer area comprises a horizontal retinal layer area and a vertical retinal layer area.

6. The retinal layer quantification system of claim 5, wherein the target image pre-processing module comprises:

a target image quality screening unit configured to screen an image quality of the target optical coherence tomographic image, so as to determine whether the target optical coherence tomographic image meets the image quality;

a target image scale bar extracting unit configured to extract a length of a scale bar of the target optical coherence tomographic image; and a target image determining unit configured to determine a position of an optic nerve of a retina in the target optical coherence tomographic image.

7. The retinal layer quantification system of claim 6, wherein the layer thickness detection module comprises:

a dividing unit configured to divide the enhanced label target image into a plurality of retinal layer thickness measurement positions, so as to output a retinal layer each region target image;

a marking unit configured to perform an edge detection analysis and mark lines on the retinal layer each region target image, so as to output a retinal layer each region marked target image; and a thickness calculating unit configured to calculate the retinal layer each region thicknesses in the retinal layer each region marked target image with the length of the scale bar extracted from the target image scale bar extracting unit.

8. The retinal layer quantification system of claim 6, wherein the layer area detection module comprises:

a segmenting unit configured to perform a horizontal retinal segmentation and a vertical retinal segmentation on the enhanced label target image to output a horizontal retinal layer target image and a vertical retinal layer target image; and an area calculating unit configured to calculate the horizontal retinal layer area in the horizontal retinal layer target image and the vertical retinal layer area in the vertical retinal layer target image with the length of the scale bar extracted from the target image scale bar extracting unit.

9. An eye care device, comprising:

the retinal layer quantification system of claim 5; and an electronic device connected to the retinal layer quantification system through telecommunication.

10. A method for detecting retinal layer thickness and retinal layer area, comprising:

providing a target optical coherence tomographic image of a subject;

providing the retinal layer quantification system of claim 5;

performing a target image pre-processing step to screen and mark the target optical coherence tomographic image using the target image pre-processing module, so as to obtain the marked target image;

performing a label target image outputting step to output the marked target image as the label target image using the retinal layer auto-segmentation model;

performing a target image enhancing step to process the label target image in an image enhancement method using the target image enhancement module, so as to obtain the enhanced label target image;

performing a layer thickness calculating step to calculate the retinal layer each region thicknesses in the enhanced label target image using the layer thickness detection module; and performing a layer area calculating step to calculate the horizontal retinal layer area and the vertical retinal layer area in the enhanced label target image using the layer area detection module.

11. The method for detecting retinal layer thickness and retinal layer area of claim 10, wherein the image enhancement method comprises an anti-Gaussian blur, an image erosion and an image dilation.

12. A method for assessing and predicting neurodegenerative disease, comprising:

providing a target optical coherence tomographic image of a subject;

providing the retinal layer quantification system of claim 5;

performing a target image pre-processing step to screen and mark the target optical coherence tomographic image using the target image pre-processing module, so as to obtain the marked target image;

performing a label target image outputting step to output the marked target image as the label target image using the retinal layer auto-segmentation model;

performing a target image enhancing step to process the label target image in an image enhancement method using the target image enhancement module, so as to obtain the enhanced label target image;

performing a calculating step to calculate the retinal layer each region thicknesses in the enhanced label target image using the layer thickness detection module and to calculate the horizontal retinal layer area and the vertical retinal layer area in the enhanced label target image using the layer area detection module;

providing a clinical test data of the subject; and comparing the clinical test data with the thickness of each area of retinal layer, the horizontal retinal layer area and the vertical retinal layer area by a regression analysis model, so as to calculate an assessing grade representing a possibility of the subject having neurodegenerative disease.

13. The method for assessing and predicting neurodegenerative disease of claim 12, wherein the clinical test data comprises a computed tomography (CT) image, an magnetic resonance imaging (MRI) image, a blood test value, a personal medical history, a family medical history, a past surgery history, a medical evaluation scale, a physiological value and a past medication habit.

\* \* \* \* \*